(12) United States Patent
Latt et al.

(10) Patent No.: US 11,617,609 B2
(45) Date of Patent: Apr. 4, 2023

(54) PERCUTANEOUS METHODS, SYSTEMS, AND DEVICES FOR POSITIONING A GUIDE WIRE IN A BONE

(71) Applicant: ARIZONA BOARD OF REGENTS ON BEHALF OF THE UNIVERSITY OF ARIZONA, Tucson, AZ (US)

(72) Inventors: L. Daniel Latt, Tucson, AZ (US); Ariana M. Nicolini, Tucson, AZ (US); Mary Coffelt, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 369 days.

(21) Appl. No.: 16/872,221

(22) Filed: May 11, 2020

(65) Prior Publication Data
US 2020/0268428 A1    Aug. 27, 2020

Related U.S. Application Data

(63) Continuation-in-part of application No. 15/204,529, filed on Jul. 7, 2016, now Pat. No. 10,646,695.
(Continued)

(51) Int. Cl.
*A61B 17/88*    (2006.01)
*A61B 17/74*    (2006.01)
*A61B 17/66*    (2006.01)

(52) U.S. Cl.
CPC .......... *A61B 17/8897* (2013.01); *A61B 17/66* (2013.01); *A61B 17/74* (2013.01)

(58) Field of Classification Search
CPC ... A61M 25/09041; A61M 2025/09116; A61B 2017/3407; A61B 2017/3403;
(Continued)

(56) References Cited

U.S. PATENT DOCUMENTS 4,292,964 A * 10/1981 Ulrich ................ A61B 17/7055
606/80
6,039,742 A * 3/2000 Krettek .............. A61B 17/1725
606/9
(Continued)

FOREIGN PATENT DOCUMENTS

CN    2524689    12/2002
CN    2857864    1/2007
(Continued)

OTHER PUBLICATIONS

Yih-Shiunn Lee, Hui-Ling Huang, Ting-Ying Lo, and Chien-Rae Huang, Dynamic hip screw in the treatment of intertrochanteric fractures: a comparison of two fixation methods. Oct. 2007; 31(5): 683-688.

*Primary Examiner* — Matthew J Lawson
(74) *Attorney, Agent, or Firm* — Nguyen Tarbet LLC

(57) ABSTRACT

Minimally invasive percutaneous methods, devices, and systems for placing guide wires in bones in a desired position and orientation and for facilitating the treatment of fractures such as but not limited to intertrochanteric fractures or other applications such as osteotomies. The methods, devices, and systems may allow for rapid and reproducible placement of a guide wire in a bone. Each degree of freedom may be controlled independently.

11 Claims, 12 Drawing Sheets

Related U.S. Application Data

(60) Provisional application No. 62/190,117, filed on Jul. 8, 2015.

(58) Field of Classification Search
CPC ............ A61B 2017/3405; A61B 17/17; A61B 17/171; A61B 17/1717; A61B 17/1721; A61B 17/1725; A61B 17/151; A61B 17/8095; A61B 17/1664; A61B 17/1742; A61B 17/175; A61B 17/1753
See application file for complete search history.

(56) References Cited

U.S. PATENT DOCUMENTS

| | | | |
|---|---|---|---|
| 6,562,042 B2 | 5/2003 | Nelson | |
| 7,507,240 B2 * | 3/2009 | Olsen ................ | A61B 17/6475 606/57 |
| 7,927,333 B2 | 4/2011 | Gradl | |
| 8,257,361 B2 | 9/2012 | Ritchey et al. | |
| 8,986,314 B1 * | 3/2015 | Jordan ............... | A61B 17/1714 606/96 |
| 11,389,223 B2 * | 7/2022 | Baskin ............... | A61B 17/1775 |
| 2009/0306679 A1 * | 12/2009 | Murphy .............. | A61K 31/409 606/130 |
| 2010/0274254 A1 * | 10/2010 | Boileau .............. | A61B 17/7098 606/62 |
| 2011/0125200 A1 | 5/2011 | Hanson et al. | |
| 2012/0150186 A1 | 6/2012 | Hajianpour | |
| 2013/0030446 A1 * | 1/2013 | Wayne ............... | A61B 17/1775 606/104 |
| 2013/0053959 A1 | 2/2013 | Lizardi et al. | |
| 2013/0197523 A1 | 8/2013 | Fitzpatrick | |
| 2015/0018719 A1 | 1/2015 | Aghazadeh | |
| 2016/0310197 A1 * | 10/2016 | Black ................. | A61B 17/92 |
| 2020/0008847 A1 * | 1/2020 | Medoff .............. | A61B 17/151 |
| 2020/0029977 A1 * | 1/2020 | Dayton .............. | A61B 17/15 |
| 2021/0052311 A1 * | 2/2021 | Fitch ................. | A61B 17/8095 |
| 2022/0183853 A1 * | 6/2022 | Smith ................ | A61F 2/446 |

FOREIGN PATENT DOCUMENTS

| | | |
|---|---|---|
| CN | 203089353 | 7/2013 |
| CN | 103393462 | 11/2013 |
| CN | 103126762 | 9/2015 |

* cited by examiner

PERCUTANEOUS METHODS, SYSTEMS, AND DEVICES FOR POSITIONING A GUIDE WIRE IN A BONE

CROSS REFERENCE

This application is a continuation-in-part and claims priority to U.S. application Ser. No. 15/204,529 filed Jul. 7, 2016, which is a non-provisional and claims priority to U.S. Patent Application No. 62/190,117 filed Jul. 8, 2015, the specifications of which are incorporated herein in their entirety by reference.

FIELD OF THE INVENTION

The present invention relates to methods, devices, and systems for placement of guide wires in bones at a desired position and orientation, for example for fractures (e.g., intertrochanteric fracture of the proximal femur), more particularly to a minimally invasive percutaneous system for accurately, rapidly, and reproducibly placing a guide wire in a bone at a desired position and orientation.

BACKGROUND OF THE INVENTION

In orthopedic surgery one often finds it necessary to place a guide wire into a bone in a desired position and orientation. These guide wires may be needed to guide an osteotomy, a drill hole, the placement of a cutting jig, etc. A common challenge is that there are often many degrees of freedom (positions and angles in multiple planes) that must be simultaneously controlled. Commonly, wire guides are placed on the bone to direct the placement of the guide wire, but this requires exposing the bone, often necessitating a large dissection. An alternative is to achieve guide wire placement using fluoroscopy with radiographic projection of an extracorporeal guide, thus avoiding the need for an incision to place the guide on bone. The challenge inherent in the use of fluoroscopy with an extracorporeal guide is the number of degrees of freedom that must be simultaneously controlled often requires multiple attempts at guide wire placement even by an experienced surgeon.

One example of an application that requires the placement of a guide wire into a bone at a precise position and orientation is the fixation of an intertrochanteric (IT) hip fracture. These fractures are commonly treated with internal fixation employing a sliding hip screw and side plate implant. Placement of the sliding hip screw is achieved using a cannulated technique in which a guide wire is drilled from the lateral femur across the femoral neck and into the femoral head. The position and orientation of the guide wire is controlled with the use of an angle guide. Typically, the angle guide is placed directly onto lateral cortex of the femur. Placement of the angle guide on the femur requires a large (e.g., 15-20 cm) incision through skin, subcutaneous tissue, fascia and muscle. A percutaneous technique (e.g., without initial incision) has been previously described and has been shown to result in less blood loss and operative time (Alobaid et al., J Orthop Trauma 18:207-212; Cheng et al., Surgical Innovation 18: 99-105; Ho et al., Int Orthop 33:555-560). However, this technique relies on freehand placement of the guide wire, which can be time consuming and technically demanding since instrumentation that would allow for the rapid, accurate, and repeatable placement of the guide wire does not exist.

In order to make the process of percutaneously placing a guide wire into bone at a desired position and orientation simple, rapid, accurate and repeatable, the present invention allows for each degree of freedom to be independently controlled and then fixed, e.g., the methods, devices, and systems of the present invention may help fix the position and/or angle of the guide wire with respect to the bone in a rapid, accurate, and repeatable manner. As a non-limiting example in the case of facilitating the treatment of an IT fracture, the methods, devices, and systems of the present invention may help fix the position and angle in the frontal and transverse planes for the guide wire used for sliding hip screw implantation. The present invention is not limited to applications related to fractures, e.g., IT fractures. The present invention may be used for any appropriate procedure or application in which a guide wire is to be placed at a prescribed position and orientation in a bone. Non-limiting examples of applications include the placement of guide pins for cannulated screws osteotomies, cutting jigs, fracture reduction and fixation, and the like. Furthermore, the devices and systems of the present invention are not limited to the particular configurations described herein. The parameters (e.g., sizes, angles, etc.), configurations, and uses of the systems and devices disclosed herein may be modified to accommodate the anatomic location and position/orientation requirements for which it is used.

Without wishing to limit the present invention to any theory or mechanism, it is believed that the systems, methods, and devices of the present invention create a minimally invasive means of properly placing a guide wire in a bone. The systems, methods, and devices of the present invention may help improve accuracy and repeatability when placing the guide wire in a bone. The systems, methods, and devices of the present invention may also help avoid putting multiple holes in the bone, which may help lessen the chance of a postoperative fracture. The systems, methods, and devices of the present invention may also help reduce incision size, surgery time, and possibly blood loss.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features percutaneous devices, systems, and methods for placing a guide wire into a bone at a desired position and orientation, wherein each degree of freedom may be controlled and/or fixed independently. There are six degrees of freedom that may be required to fully specify the position and orientation of a body in 3D space. There are a number of ways to represent these six degrees of freedom. One way is to specify three positions and three angles. In orthopedic surgery, these degrees of freedom are often specified relative to the anatomic axes of the limb. One example of such set is three angles (flexion/extension, varus/valgus, and internal/external rotation) and three positions (superior/inferior, anterior/posterior, and medial/lateral).

The present invention features an external guide system for placing a guide wire into a bone at a particular position and orientation. In some embodiments, the system comprises an alignment plate; at least a first wing extending downwardly from a first side of the alignment plate, wherein the first wing is adapted to directly or indirectly position and hold a placement pin; a slide bar slidably engaged in a channel disposed in the alignment plate, wherein the slide bar extends downwardly from the alignment plate and the slide bar can slide in at least a first direction toward a first end of the alignment plate and a second direction toward a second end of the alignment plate; and a guide wire grip adapted to position and hold a guide wire. In some embodiments, the guide wire grip is pivotally attached to a guide wire grip base wherein the guide wire grip can pivot within the guide wire grip base in a first direction toward the alignment plate and a second direction opposite the first direction. In some embodiments, the guide wire grip base is slidably attached to the slide bar such that it can slide in a first direction toward the alignment plate and a second direction opposite the first direction. The system is adapted to allow independent positioning of flexion-extension angle, varus-valgus angulation, internal-external rotation angle, superior-inferior position, anterior-posterior position, and medial-lateral position of the guide wire.

In some embodiments, the system further comprises a second wing extending downwardly from a second side of the alignment plate opposite the first side, wherein the second wing is adapted to directly or indirectly accept a placement pin. In some embodiments, the first wing and the second wing are separated by a distance.

In some embodiments, the system comprises a positioning pin grip adapted to position and hold a positioning pin directly or indirectly slidably attached to the first wing, wherein the positioning pin grip can be slid in a first direction toward the alignment plate and a second direction opposite the first direction. In some embodiments, the positioning pin grip is attached to a positioning pin grip base, which is slidably attached to the first wing, wherein the positioning pin grip base slides in a first direction toward the alignment plate and a second direction opposite the first direction. In some embodiments, the positioning pin grip comprises a positioning pin grip slot adapted to accept a positioning pin.

In some embodiments, the first wing comprises a plurality of holes disposed therethrough that allow passage of a placement pin, wherein the holes are at a first hole angle with respect to the length of the first wing and at a second hole angle with respect to the width of the first wing. In some embodiments, the second wing comprises a plurality of holes disposed therethrough that allow passage of a placement pin, wherein the holes are at a first hole angle with respect to the length of the second wing and at a second hole angle with respect to the width of the second wing. In some embodiments, the first hole angle is from 20 to 90 degrees and the second hole angle is from 20 to 90 degrees. In some embodiments, the slide bar slidably engages the channel via a connector.

In some embodiments, the slide bar comprises a guide wire grip shaft, wherein the guide wire grip base is slidably attached to the guide wire grip shaft and can slide in the first direction and second direction along the slide bar via the guide wire grip shaft. In some embodiments, the guide wire grip base engages a slot is disposed in the slide bar, wherein the slot extends along at least a part of a length of the slide bar. In some embodiments, the guide wire grip comprises a guide wire grip slot adapted to accept a guide wire, wherein a guide wire can slide within the guide wire grip slot in a first direction and second direction opposite the first direction. In some embodiments, the guide wire grip comprises one more guide wire grip holes adapted to accept a guide wire.

In some embodiments, the system further comprises an alignment bar disposed on or in the alignment plate; the alignment bar is a guide for placing the alignment plate on a subject.

In some embodiments, the system is for placing a guide wire into a bone for facilitating treatment of a fracture or an osteotomy.

The present invention also features methods for positioning a guide wire into a bone at a particular position and orientation. In some embodiments, the method comprises placing an external guide system of the present invention atop a treatment area of a subject, positioning at least one placement pin directly or indirectly in the first wing and further into the bone to secure the external angle guide system in place; positioning the slide bar to an appropriate position within the channel; and inserting a guide wire through the guide wire grip and further into a bone.

In some embodiments, the method further comprises pivoting the guide wire grip within the guide wire grip base to help position the guide wire. In some embodiments, the method further comprises sliding the guide wire grip base on the slide bar to help position the guide wire. In some embodiments, the method further comprises securing the slide bar in the channel via a locking component. In some embodiments, the method is for facilitating the treatment of a fracture or an osteotomy.

The present invention also features an external guide system comprising: an alignment plate; a first wing and a second wing both extending downwardly from the alignment plate on opposite sides; a positioning pin grip slidably attached to each wing, the positioning pin grips can be slid in a first direction toward the alignment plate and a second direction opposite the first direction, wherein each positioning pin grip comprises a positioning pin grip slot adapted to accept a placement pin; a slide bar slidably engaged in a channel disposed in the alignment plate, the slide bar extends downwardly from the alignment plate, the slide bar can slide in at least a first direction toward a first end of the alignment plate and a second direction toward a second end of the alignment plate; a guide wire grip with a guide wire grip slot disposed therein adapted to position and hold a guide wire, the guide wire grip is pivotally attached to a guide wire grip base wherein the guide wire grip can pivot within the guide wire grip base in a first direction toward the alignment plate and a second direction opposite the first direction, wherein the guide wire grip base is slidably attached to a guide wire grip shaft disposed on the slide bar such that it can slide in a first direction toward the alignment plate and a second direction opposite the first direction. The system is adapted to allow independent positioning of flexion-extension angle, varus-valgus angulation, internal-external rotation angle, superior-inferior position, anterior-posterior position, and medial-lateral position of the guide wire.

In some embodiments, a percutaneous device for placing a guide wire in a bone comprises an external guide system. In some embodiments, the system comprises an alignment plate, wherein an alignment bar (e.g., a linear or nearly linear alignment bar) is disposed in or on a top surface of the alignment plate; at least a first wing that extends downwardly from a first side of the alignment plate, wherein the first wing is adapted to allow passage of a placement pin therethrough at a first hole angle with a length of the first wing and at a second hole angle with respect to a width of the first wing; and a slide bar slidably engaged in a channel disposed in the top surface of the alignment plate, wherein the slide bar extends downwardly from the alignment plate and the slide bar can slide in at least a first direction toward a first end of the alignment plate and a second direction toward a second end of the alignment plate. In some embodiments, a slot is disposed in the slide bar extending along at least a part of a length of the slide bar, wherein the slot is adapted to accept a guide wire. The slot may be at an angle with respect to a width of the slide bar.

In some embodiments, the alignment plate is a femoral alignment plate. In some embodiments, the guide wire is a central guide wire.

In some embodiments, the alignment bar is perpendicular to the length of the alignment plate. In some embodiments, the alignment bar extends from at or near a first end to at or near a second end of the alignment plate. In some embodiments, the alignment bar comprises a groove, an indentation, a protrusion, a marking, or a combination thereof. In some embodiments, the system further comprises a second wing that extends downwardly from the first side of the alignment plate, wherein the second wing is adapted to allow passage of a placement pin therethrough at a first hole angle with respect to a length of the second wing and at a second hole angle with respect to a width of the second wing. The first wing and the second wing may be separated by a distance.

In some embodiments, the first wing comprises a plurality of holes disposed therethrough that allow passage of a placement pin, wherein the holes are at a first hole angle with respect to the length of the first wing and at a second hole angle with respect to the width of the first wing. In some embodiments, the second wing comprises a plurality of holes disposed therethrough that allow passage of a placement pin, wherein the holes are at a first hole angle with respect to the length of the second wing and at a second hole angle with respect to the width of the second wing. In some embodiments, the channel extends from at or near the first end to at or near the second end of the alignment plate. In some embodiments, the slide bar slidably engages the channel via a connector. In some embodiments, the system further comprises a locking component adapted to secure the slide bar in a position with respect to the channel. In some embodiments, the slide bar comprises more than one slot. In some embodiments, the slide bar is removable.

The present invention also features methods of facilitating the treatment of a fracture (e.g., an IT fracture). In some embodiments, the method comprises placing an external angle guide system according to the present invention atop a leg of a patient; aligning the alignment bar with a femur of the patient; driving at least one placement pin through the first wing and further into the femur to secure the external angle guide system in place; positioning the slide bar to an appropriate position; inserting a guide wire through the slot and further into the femoral head of the femur; and implanting a dynamic hip screw into the femur. In some embodiments, the method further comprises securing the slide bar in the channel via a locking component.

The present invention also features a method of placing a guide wire (e.g., a central guide wire) into a bone at a desired position and orientation, wherein each degree of freedom may be controlled and/or fixed independently. In some embodiments, the method comprises placing an external angle guide system according to the present invention atop a treatment area of a patient. In some embodiments, the treatment area of the patient is the leg, e.g., thigh area. The present invention is not limited to applications related to leg and hip bones. As such, the treatment area of the patient may be any appropriate area wherein a guide wire is to be inserted into a bone. The method may further comprise aligning the alignment bar with a bone (e.g., femur) of the patient and driving at least one placement pin through the first wing and further into the bone (e.g., femur) to secure the external angle guide system in place. The method may further comprise positioning the slide bar at an appropriate position. In some embodiments, the method further comprises securing the slide bar in the channel via a locking component. The method further comprises inserting a guide wire through the slot and further into the bone.

As an example (e.g., in a case of facilitating the treatment of an IT fracture), in some embodiments, the method (percutaneous method) of placing a guide wire into a bone at a desired position and orientation comprises one or more of the steps: placing a guide system (e.g., an external guide system of the present invention) on the patient's thigh, aligning a guide system (e.g., an external guide system) in the frontal plane (varus/valgus), fixing the guide system to the femur, selecting the superior/inferior position and fixing it, selecting the transverse plane angulation (internal/external rotation) fixing it, and selecting the sagittal plane position (anterior/posterior). The present invention is not limited to applications related to facilitating the treatment of an IT fracture, and the steps of the methods of the present invention may be modified as appropriate for the application.

BRIEF DESCRIPTION OF THE DRAWINGS

The patent application or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which.

DETAILED DESCRIPTION OF THE INVENTION

Figure 1A:
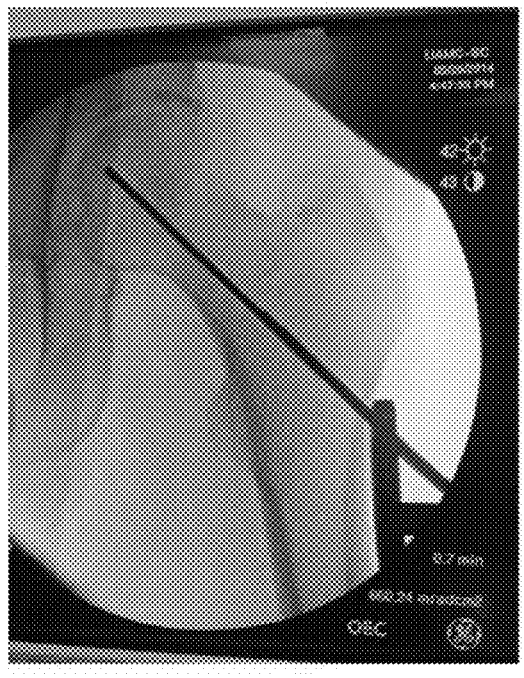
FIG. 1A (prior art) shows a DHS angle guide with a guide wire held up over the thigh aligned with a pin that is in the femur.
Figure 1B:
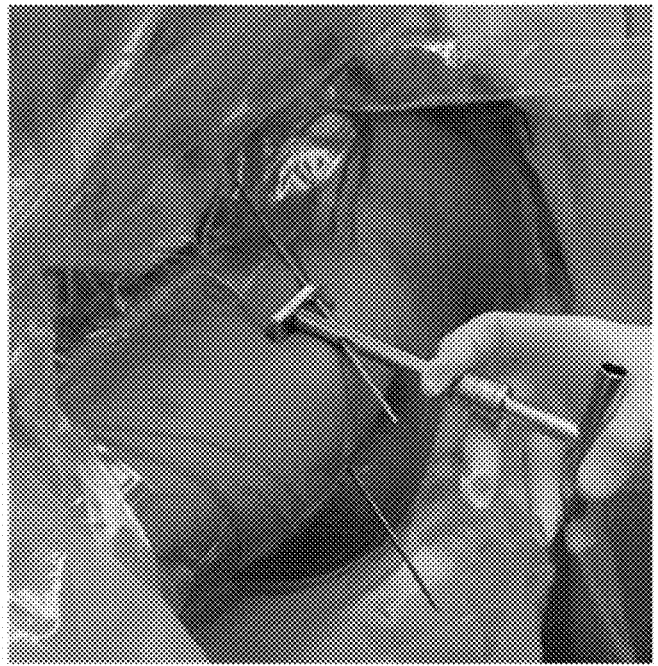
FIG. 1B (prior art) shows a fluoroscopic image of the freehand placement of the guide wire shown in 1A.

Following is a list of elements corresponding to a particular element referred to herein:

- 50 femur
- 100 external angle guide system
- 102 guide wire (e.g., central guide wire)
- 103 DHS angle guide (prior art)
- 105 positioning pin
- 106 parallel guide pin
- 107 upper angle guide pin
- 110 alignment plate (e.g., femoral alignment plate)
- 111 first end of alignment plate
- 112 second end of alignment plate
- 113 first side of alignment plate
- 114 second side of alignment plate
- 115 top surface of alignment plate
- 116 upper angle guide
- 118 alignment bar
- 120 wing
- 120a first wing
- 120b second wing
- 120c first wing channel
- 120d second wing channel
- 121 bottom end of wing
- 122 top end of wing
- 123 inner surface of wing
- 124 outer surface of wing
- 125 first side of wing
- 126 second side of wing
- 128 holes (e.g., channels through wings)
- 129a first hole angle
- 129b second hole angle
- 130 channel
- 140 slide bar
- 141 first side of slide bar
- 142 second side of slide bar
- 144 outer surface of slide bar
- 144 locking component
- 145 connector hole
- 148 connector
- 150 slot
- 159 slot angle
- 160 guide wire grip
- 162 guide wire grip slot
- 164 guide wire grip shaft
- 166 guide wire grip base
- 168 guide wire grip hole
- 169 guide wire grip base channel
- 170 positioning pin grip
- 172 positioning pin grip slot
- 176 positioning pin grip base
- 182 tightening screw hole
- 184 gripping component
- 188 screw fixation track
- 240 additional guiding component
- 248 additional locking component
- 268 additional guide wire hole
- 270 additional pre-positioning component Referring now to FIG. 1A and FIG. 1B, as previously discussed, current methods of treating stable intertrochanteric (IT) hip fractures include using a dynamic hip screw (DHS) comprising a dynamic compression plate (DCP) with a barrel and an intramedullary screw (DHS screw). Implantation of the DHS requires the placement of a DHS angle guide (103) directly on the femur so that the guide wire (102) (or guide pin) can be inserted. The guide wire (or guide pin) must be placed in the center of the femoral head at the correct angle. FIG. 1A shows a DHS angle guide (103) with a guide wire held up over the thigh aligned with a pin that is in the femur, and FIG. 1B shows a fluoroscopic image of the freehand placement of the guide wire (102) shown in 1A.

Referring now to FIG. 2-7, the present invention features percutaneous methods, devices, and systems for positioning a guide wire (102) in a bone at a desired position and orientation, wherein each degree of freedom may be controlled independently. For example, the present invention features methods of facilitating the treatment of fractures (fractures may include but are not limited to IT fractures), wherein the methods utilize guide systems (100) described herein. As an example related to IT fractures, an external angle guide system (100) of the present invention may be positioned on top of the patient's leg. The external angle guide system (100) of the present invention allows for accurate and rapid placement of a guide wire (102) without the need of a large (e.g., 15 to 20 cm) surgical incision. In some embodiments, the guide wire (102) is a central guide wire.

The guide systems (100) of the present invention are not limited to the components, configurations, and uses described herein.

Figure 2A:
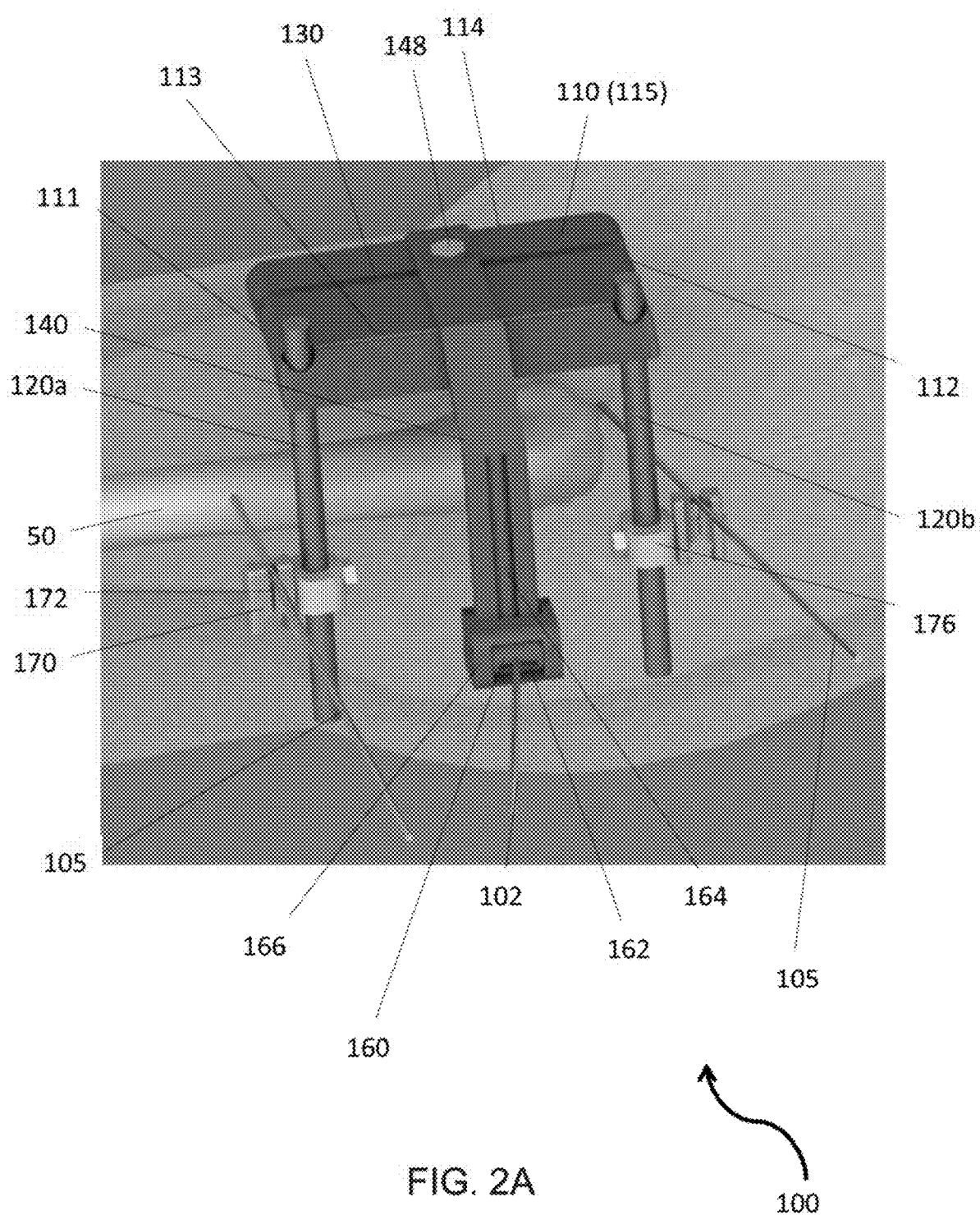
FIG. 2A shows an in-use view of an embodiment of an external angle guide system of the present invention.
Figure 2B:
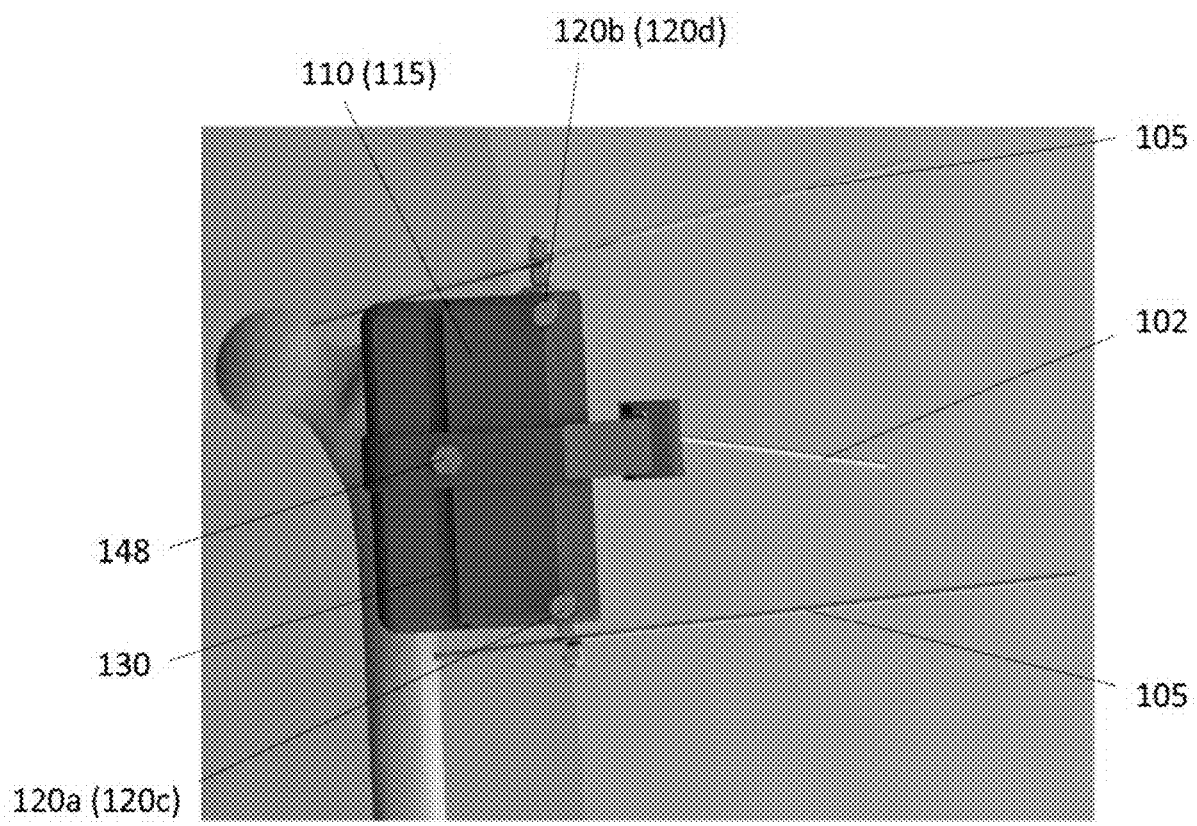
FIG. 2B shows a top view and in-use view of the external angle guide system of FIG. 2A.
Figure 2C:
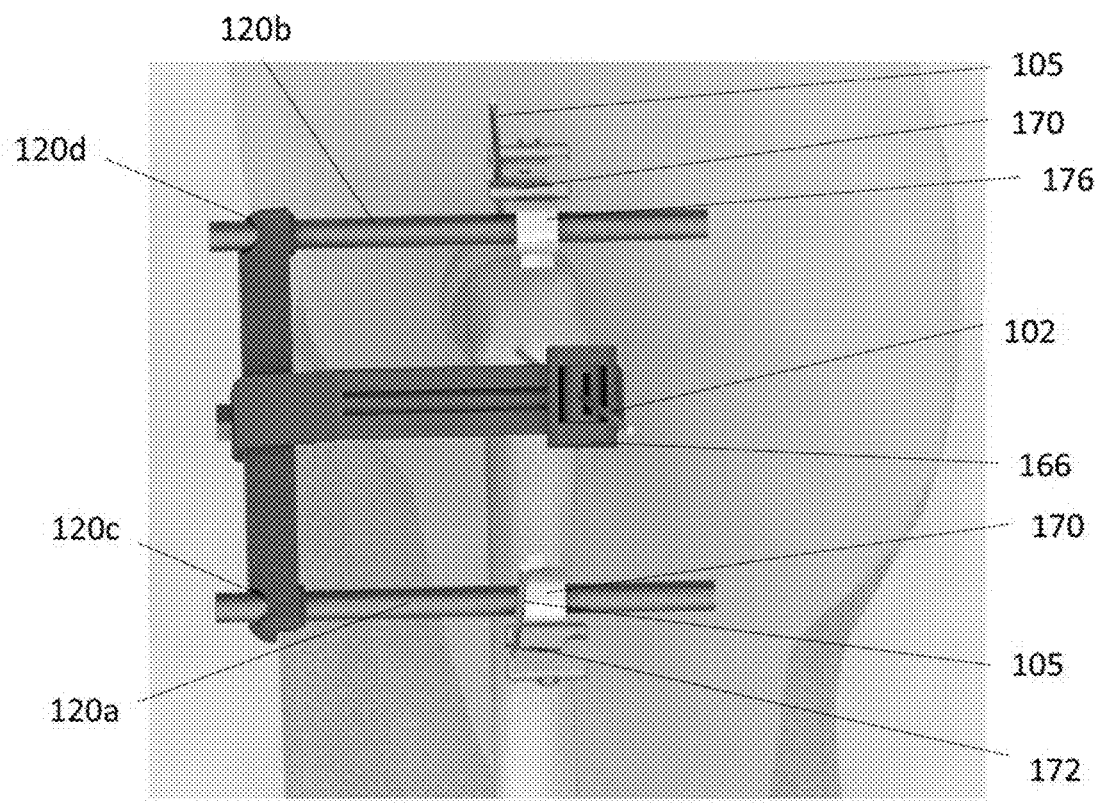
FIG. 2C shows a side view and in-use view of the external angle guide system of FIG. 2A.

As shown in FIG. 2A, FIG. 2B, and FIG. 2C, the external guide system (100) of the present invention comprises an alignment plate (110) (e.g., a femoral alignment plate). For clarity with respect to the drawings, the alignment plate (110) comprises a first end (111), a second end (112) opposite the first end (111), a first side (113) (e.g., a front end if viewed as in FIG. 2A), a second side (114) opposite the first side (113), a top surface (115), and a bottom surface; however, these distinctions are not meant to limit the system (100) in any way. In some embodiments, for example for applications related to facilitating the treatment of an IT fracture, the alignment plate may be for placing atop the patient's leg, e.g., atop the quadriceps area. Note the present invention is not limited to the treatment of IT fractures. Also, while the examples shown in FIG. 2A, FIG. 2B, and FIG. 2C show the system (100) placed atop a patient's leg for guide pin insertion into the femur (50), the present invention is not limited to placement over or near the femur (50).

In some embodiments, the system (100) further comprises one or more wings that extend from the first side (113) (e.g., downwardly) from the first side (113) of the alignment plate (110), e.g., the wings being positioned on opposite sides of the alignment plate (110). In some embodiments, the wings (120) resemble shafts or cylinders, however the wings are not limited to a shaft or cylindrical configuration. The system (100) may comprise a first wing (120*a*) and a second wing (120*b*) that extend downwardly (or downwardly and outwardly) from the first side (113) of the alignment plate (110). The first wing (120*a*) may be positioned at or near the first end (111) of the alignment plate (110), and the second wing (120*b*) may be positioned at or near the second end (112) of the alignment plate (110). The wings (120) may be spaced a distance apart (e.g., as shown in FIG. 2A). In some embodiments, the wings (120) extend through wing channels in the alignment plate (110), e.g., the first wing (120*a*) extends through a first wing channel (120*c*) in the alignment plate (110), the second wing (120*b*) extends through a second wing channel (120*d*) in the alignment plate (110). In some embodiments, the wings (120) are perpendicular to the alignment plate (110). In some embodiments the wings (120) are at an angle with respect to the alignment plate (110), the angle being less than 90 degrees. In some embodiments, the wings (120) are at an angle with respect to the alignment plate (110), the angle being more than 90 degrees.

Slidably disposed on each wing (120) is a positioning pin grip (170) adapted to secure a positioning pin (105) in a particular location and orientation. In some embodiments, the positioning pin grip (170) is connected (slidably) to the wing (120) via a positioning pin grip base (176). The positioning pin grip base (176) may slide in a first direction and a second direction (e.g., upwardly, downwardly) along the wing (120) and may be secured in a particular position via a securing component. In some embodiments, the positioning pin grip base (176) functions as a clamp around the wing (120) (e.g., tightening the positioning pin grip base (176) may secure the positioning pin grip base (176) in place with respect to the wing (120)); however the positioning pin grip base (176) is not limited to this configuration. The positioning pin grip (170) comprises a positioning pin grip slot (172) adapted to accept a positioning pin (105). The positioning pin (105) may be secured within the positioning pin grip slot (172) via a securing component. In some embodiments, the positioning pin grip (170) (with slot (172)) functions as a clamp around the positioning pin (105) (e.g., tightening the positioning pin grip (170) may secure the positioning pin (105) in place with respect to the positioning pin grip slot (172)); however the positioning pin grip (170) is not limited to this configuration.

In some embodiments, the system (100) further comprises a slide bar (140) with a connector (148) that is adapted to engage with and slide in a channel (130) disposed in the top surface (115) of the alignment plate (110). (In some embodiments, a channel (130) may extend from at or near the first end (111) to at or near the second end (112) of the alignment plate (110). In some embodiments, the channel (130) extends through only a portion of the top surface (115) of the alignment plate (110).) As shown in FIG. 2A, the slide bar (140) extends downwardly from the alignment plate (110), e.g., similar to the extension downwardly of the wings (120), though the positioning of the slide bar (140) is not limited to the positioning or direction of the wings (120)). In some embodiments, the slide bar (140) can slide in at least a first direction toward the first end (111) of the alignment plate (110) and/or the first wing (120*a*) and a second direction toward the second end (112) of the alignment plate (110) and/or the second wing (120*b*). In some embodiments, the wings (120) limit the distance the sliding bar (140) can slide. In some embodiments, the slide bar (140) comprises a connector (148), which slidably engages the channel (130). In some embodiments, the slide bar (140) further comprises a locking component for securing the slide bar (140) in place within the channel (130). In some embodiments, the locking component is integrated into the connector (148), e.g., the connector (148) functions as a locking component to temporarily secure the slide bar (140) in a particular place.

As shown in FIG. 2A, FIG. 2B, and FIG. 2C, in some embodiments, a guide wire grip (160) is disposed on the slide bar (140). The guide wire grip (160) functions to secure a guide wire (102) in a particular position and orientation. In some embodiments, the guide wire grip (160) comprises a guide wire grip slot (162) adapted to accept a guide wire (102). In some embodiments, a guide wire (102) can slide in a first direction and second direction (e.g., side to side as viewed from the direction shown in FIG. 2A) within the guide wire slot (162). The guide wire grip (160) may be pivotally or rotatably attached to the slide bar (140) via a guide wire grip base (166). In some embodiments, the guide wire grip (160) can pivot in a first direction and second direction (e.g., upwardly, downwardly as viewed from the direction shown in FIG. 2A) with respect to the guide wire grip base (166). In some embodiments, the guide wire grip base (166) is slidably attached to the slide bar (140). For example, in some embodiments, a guide wire grip shaft (164) is disposed on the slide bar (140), and the guide wire grip base (166) is slidably attached to the guide wire grip shaft (164). In some embodiments, the guide wire grip base (166) can slide upwardly and downwardly along the guide wire grip shaft (164). The movement of the slide bar (140) along the channel (130), the movement of the guide wire grip base (166) along the guide wire grip shaft (164) of the slide bar (140), the pivoting of the guide wire grip (160) in the guide wire grip base (166), and the movement of the guide wire (102) in the guide wire grip slot (162) allow for many different positions, angles, and orientations of the guide wire with respect to the patient and the area of interest.

In some embodiments, a securing component or the slide bar (140) itself can temporarily secure the slide bar (140) in a position (e.g., desired position) with respect to the channel (130). In some embodiments, a securing component or the guide wire grip base (166) itself can temporarily secure the guide wire grip base (166) in a position (e.g., a desired position) with respect to the guide wire grip shaft (164) of the slide bar (140). In some embodiments, a securing component of the guide wire grip (160) itself can temporarily secure the guide wire grip (160) in a position (e.g., a desired position) with respect to the guide wire grip base (166). In some embodiments, a securing component or the guide wire grip slot (162) itself can temporarily secure the guide wire (102) in a position (e.g., a desired position) with respect to the guide wire grip slot (162).

Figure 3:
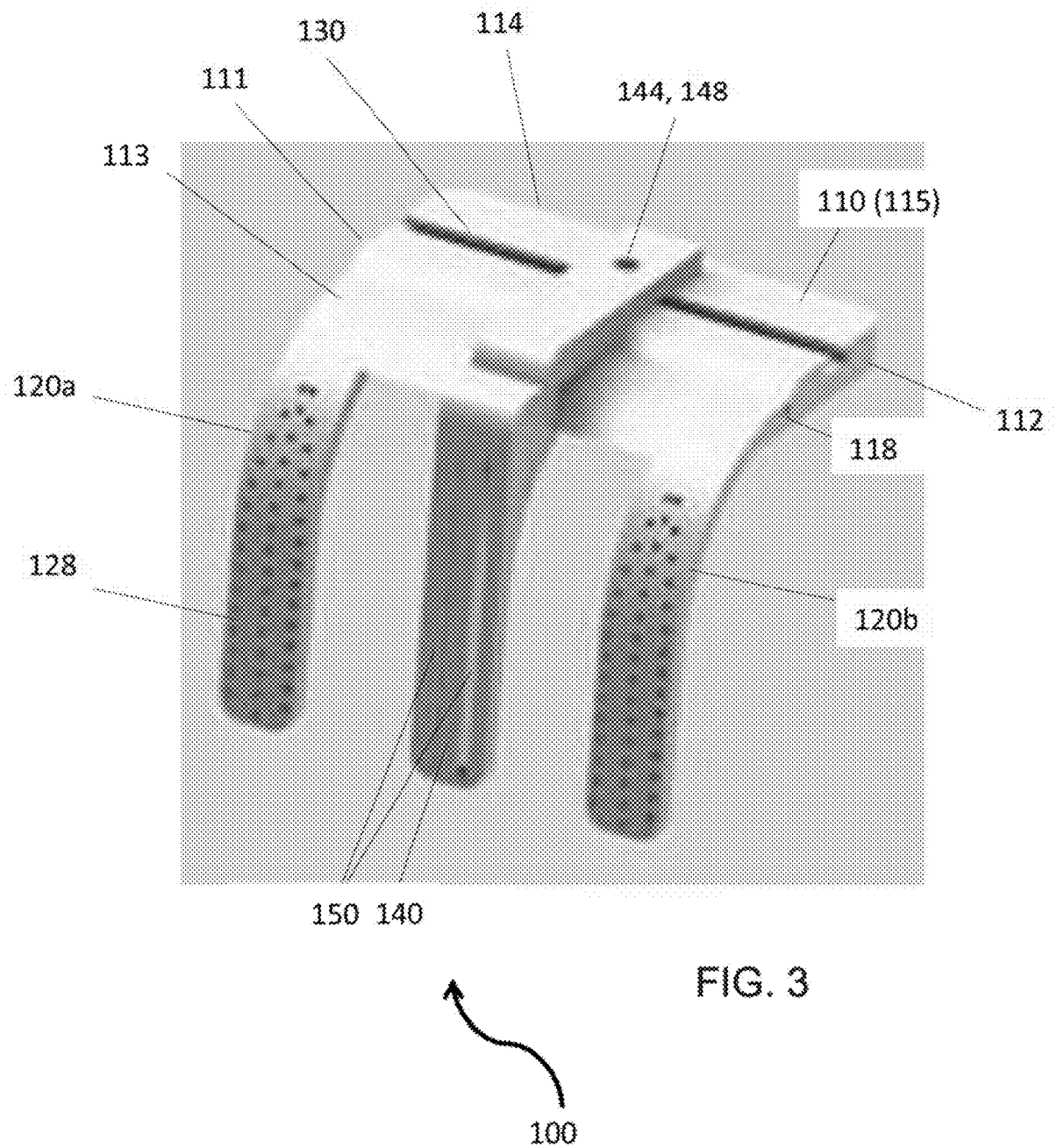
FIG. 3 shows a perspective view of an alternative embodiment of an external angle guide system of the present invention.
Figure 4A:
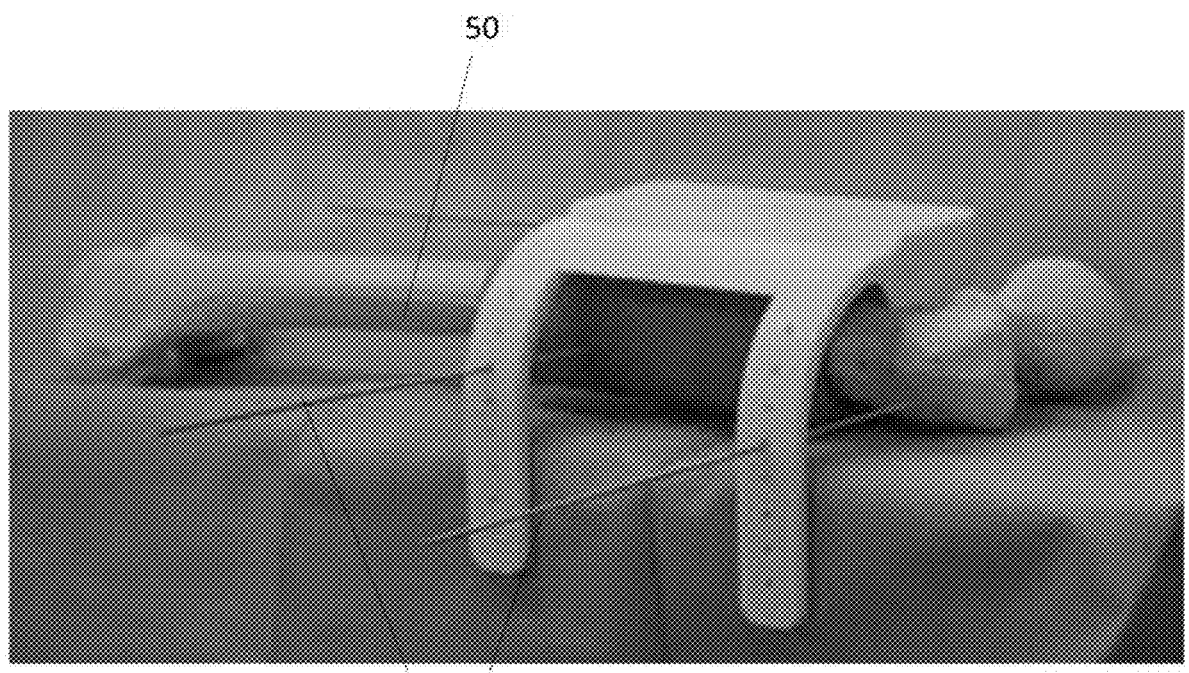
FIG. 4A and FIG. 4B show the placement of an external angle guide (such as that of FIG. 3) on an artificial femur. Athletic tape was used to mock the skin and muscle atop the artificial femur. Note: A slide bar is not shown in FIG. 4A and FIG. 4B.
Figure 4B:
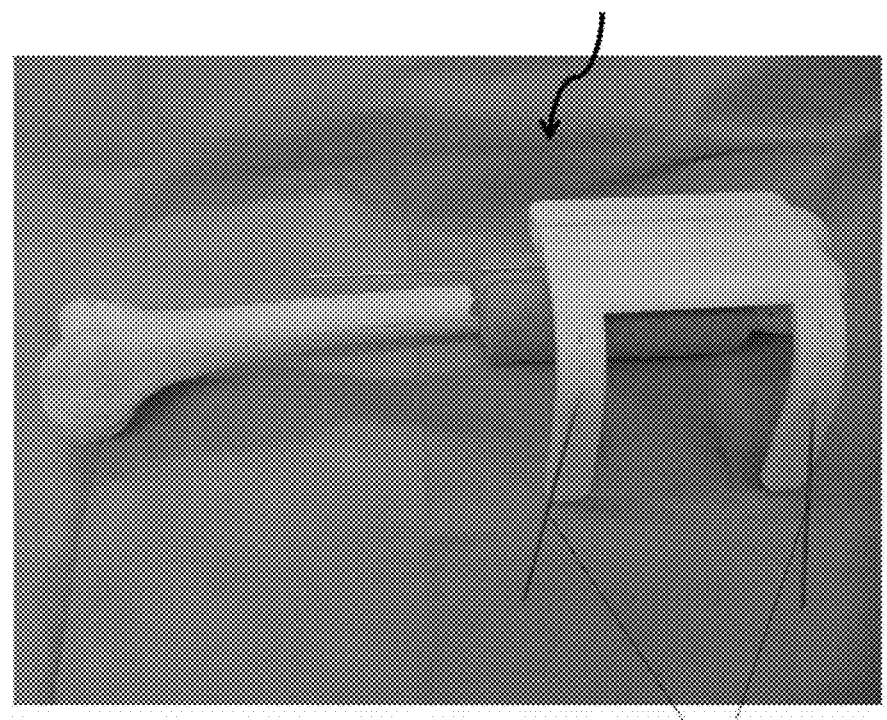

As shown in FIG. 3, FIG. 4A, and FIG. 4B, an alternative embodiment of the external guide system (100) of the present invention comprises an alignment plate (110) (e.g., a femoral alignment plate). For clarity with respect to the drawings, the alignment plate (110) comprises a first end (111), a second end (112) opposite the first end (111), a first side (113), a second side (114) opposite the first side (113), a top surface (115), and a bottom surface; however, these distinctions are not meant to limit the system (100) in any way. In some embodiments, the system (100) further comprises one or more wings that extend from the first side (113), e.g., outwardly and downwardly from the first side (113), of the alignment plate (110). For example, the system (100) may comprise a first wing (120a) and a second wing (120b) that extend outwardly and downwardly from the first side (113) of the alignment plate (110). In some embodiments, the intersection of the wings (120), e.g., the top end (121) of the wings (120), and the side (113) of the alignment plate (110) is curved, e.g., as shown in FIG. 3. However, the system (100) is not limited to this configuration, e.g., the wings (120) (e.g., the top ends (121) of the wings (120)) and alignment plate (110) (e.g., the first side (113) of the alignment plate (110)) may join at a right angle, for example. In some embodiments, the first wing (120a) is positioned at or near the first end (111) of the alignment plate (110). In some embodiments, the second wing (120b) is positioned at or near the second end (112) of the alignment plate (110). In some embodiments (e.g., in some cases related to facilitating the treatment of IT fractures), when the system (100) is in use, the wings (120) extend downwardly from the quadriceps area. In some embodiments, the wings (120) are separated by a distance. For clarity with respect to the drawings, the wings (120) have a top end (121), a bottom end (122) opposite the top end (121), a first side (125), a second side (126) opposite the first side (125), an outer surface (123), and an inner surface (124); however, these distinctions are not meant to limit the system (100) in any way.

Disposed in the wings (120) is a plurality of holes (128) (or channels through the wings). Without wishing to limit the present invention to any theory or mechanism, it is believed that the particular configuration of the holes may not necessarily be as important as the ability to rigidly fix to the bone (e.g., femur).

In some embodiments, the holes (128) extend from the outer surface (123) of the wing (120) to the inner surface (125) of the wing (120) (the inner surface (125) referring to the surface that contacts the patient), e.g., forming a channel. The holes (128) may be placed at an angle with respect to the outer surface (124) and/or inner surface (124) of the wing (120). The holes (128) may be configured in rows and/or columns. The holes (128) may be configured in pairs that are aligned in rows (e.g., a first hole is disposed in the first wing and a second hole is disposed in the second wing, and the two holes are aligned with one another with respect to the position along the length/height of the wing). The holes (128) are adapted to accept placement pins (105), e.g., placement pins (105) for inserting into the bone, e.g., the femur (e.g., see FIG. 4A, FIG. 4B). In some embodiments, the holes of the pairs may be at different angles. However, the present invention is not limited to this configuration and the holes of the pair may be constructed at similar angles. The placement pins (105) are adapted to help secure the external angle guide system (100) of the present invention in place. Without wishing to limit the present invention to any theory or mechanism, holes having different angles may be useful for helping to secure the system (100) in place, e.g., the placement pins being at different angles may be more secure. In some embodiments, a user can choose two holes that are at two different angles, but the holes are not necessarily considered to be a pair (e.g., on the exact same row). The pairs of holes (e.g., channels through the wings) may be constructed having different angles. The wings are not limited to a single column of holes, e.g., the wings may have one, two, three, or more than three columns of holes.

In some embodiments, the wings (120) do not necessarily have holes but are constructed from one or more materials that allow for penetration with a positioning pin (105) and also allow for holding the positioning pin (105) in place once inserted. For example, the wings (120) may be constructed from one or more materials that are soft enough to be penetrated by the positioning pin (105) but firm enough to hold the positioning pin (105) in place once inserted therein. Other configurations may be contemplated; for example, in some embodiments, rods are used in lieu of wings (and optionally external fixator pins are used, optionally pinning to bar clamps, etc.).

Figure 5A:
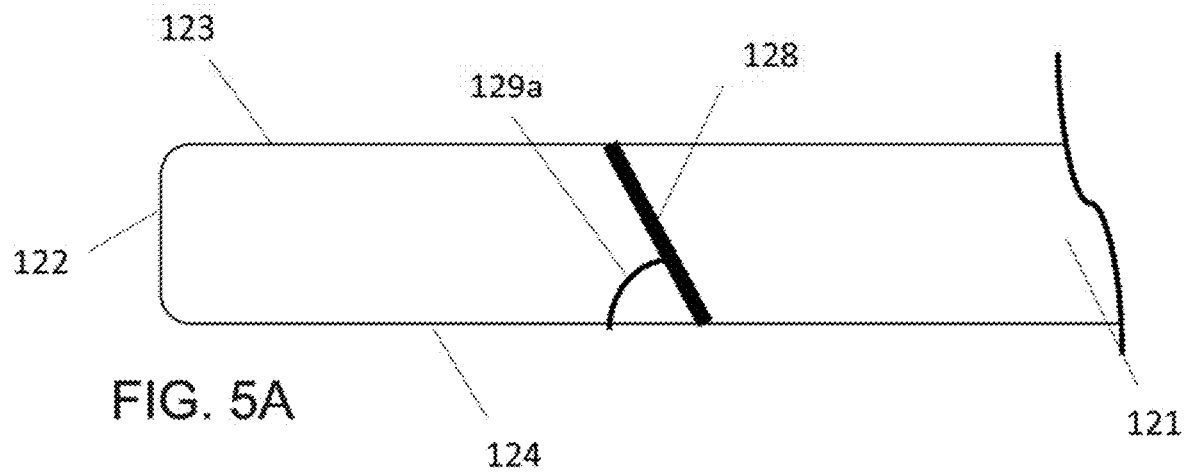
FIG. 5A is a side view of a wing, illustrating a hole at an angle with respect to the outer surface of the wing (as shown along the length of the wing from the top end to the bottom end).
Figure 5B:
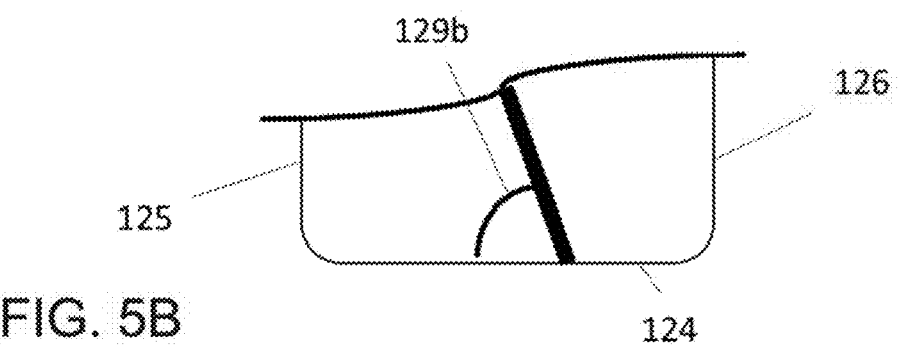
FIG. 5B is a top view of a wing, illustrating a hole at an angle with respect to the outer surface of the wing (as shown along the width of the wing from the first side to the second side).

In some embodiments, the holes (128) in the wings (120) are at an angle with respect to the wings (120), e.g., the outer surfaces (124) of the wings (120). As shown in FIG. 5A, the holes (128) are at a first hole angle (129a) with respect to the length of the wing (120), e.g., the outer surface (124) along its length as viewed from the top end (121) to the bottom end (122) of the wing. Note that the first hole angle is the smaller of the two angles formed, e.g., the first hole angle may be X degrees, and its opposite angle is 180−X, wherein X is 90 or less. As shown in FIG. 5B, the holes (128) are at a second hole angle (129b) with respect to the width of the wing (120), e.g., the outer surface (124) along its width as viewed from the first side (125) to the second side (122) of the wing (120). Note that the second hole angle is the smaller of the two angles formed, e.g., the second hole angle may be X degrees, and its opposite angle is 180−X, wherein X is 90 or less.

In some embodiments, the first hole angle (129a) is from 10 to 90 degrees. In some embodiments, the first hole angle (129a) is from 20 to 90 degrees. In some embodiments, the first hole angle (129a) is from 30 to 90 degrees. In some embodiments, the first hole angle (129a) is from 40 to 90 degrees. In some embodiments, the first hole angle (129a) is from 50 to 90 degrees. In some embodiments, the first hole angle (129a) is from 60 to 90 degrees. In some embodiments, the first hole angle (129a) is from 70 to 90 degrees. In some embodiments, the first hole angle (129a) is from 80 to 90 degrees.

In some embodiments, the second hole angle (129b) is from 10 to 90 degrees. In some embodiments, the second hole angle (129b) is from 20 to 90 degrees. In some embodiments, the second hole angle (129b) is from 30 to 90 degrees. In some embodiments, the second hole angle (129b) is from 40 to 90 degrees. In some embodiments, the second hole angle (129b) is from 50 to 90 degrees. In some embodiments, the second hole angle (129b) is from 60 to 90 degrees. In some embodiments, the second hole angle (129b) is from 70 to 90 degrees. In some embodiments, the second hole angle (129b) is from 80 to 90 degrees.

The wings (120) may each comprise one or more or a plurality of holes, and the holes may be at similar or different angles with respect to the outer surface (124) of the wing (120).

In some embodiments, an alignment bar (118) (e.g., a linear marking, groove, indentation, protrusion, etc.) is disposed in the top surface (115) of the alignment plate (110). In some embodiments, the alignment bar (118) extends from at or near the first end (111) to at or near the second end (112). In some embodiments, the alignment bar (118) extends through only a portion of the top surface (115) of the alignment plate (110). In some embodiments, the alignment bar (118) is intended to serve as a guide for placement of the system (100), wherein the alignment bar (118) is for aligning with the femur of the patient. In some embodiments, the alignment bar (118) is a groove or indentation. In some embodiments, the alignment bar (118) is a protrusion. In some embodiments, the alignment bar is a marking on the alignment plate (110).

A channel (130) may be disposed in the top surface (115) of the alignment plate (110). The channel (130) may extend from at or near the first end (111) to at or near the second end (112) of the alignment plate (110). In some embodiments, the channel (130) extends through only a portion of the top surface (115) of the alignment plate (110).

In some embodiments, the system (100) further comprises a slide bar (140) with a connector (148) that is adapted to engage with and slide in the channel (130). The slide bar (140) extends downwardly, e.g., similar to the extension direction of the wings (120) (though not limited to the extension direction of the wings). The slide bar (140) can slide in at least a first direction toward the first end (111) of the alignment plate (110) and/or the first wing (120a) and a second direction toward the second end (112) of the alignment plate (110) and/or the second wing (120b). In some embodiments, the wings (120) limit the distance the sliding bar (140) can slide. In some embodiments, the slide bar (140) comprises a locking component (144) for securing the slide bar (140) in place within the channel (130). In some embodiments, the locking component (144) is integrated into the connector (148), e.g., the connector (148) functions as a locking component.

A slot (150) (or two slots, or more than two slots) may be disposed in the slide bar (140) extending from the outer surface and through the inner surface (the inner surface being the surface facing the patient) and may run along part or all of the length of the slide bar (140), e.g., from near the top of the slide bar to near the bottom of the slide bar (140). The slot (150) is adapted to accept the guide wire (102). The slot (150) may be configured to help insert the guide wire (102) appropriately, e.g., to position and angle the guide wire (120) appropriately.

Figure 5C:
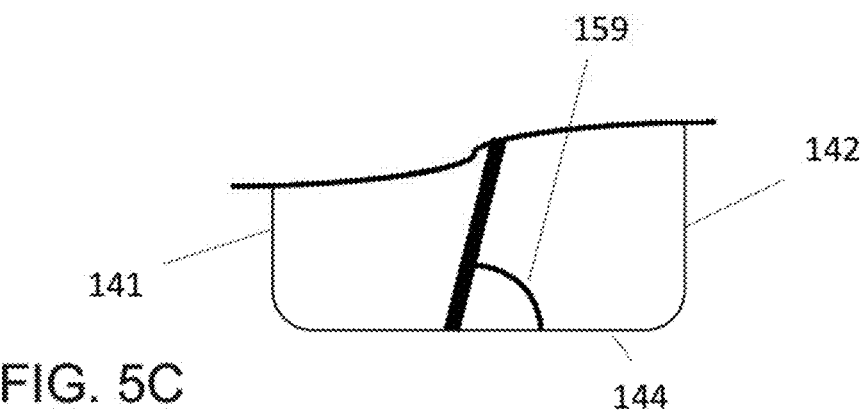
FIG. 5C is a top view of the slide bar, illustrating a slot at an angle with respect to the outer surface of the slide bar (as shown along the width of the slide bar from the first side to the second side).

In some embodiments, the slot (150) is at a slot angle (159) with respect to the width of the slide bar (140), e.g., the outer surface (144) of the slide bar (140) along its width, e.g., as viewed from the first side (141) to the second side (142) of the slide bar (140) (see FIG. 5C). Note that the slot angle (159) is the smaller of the two angles formed, e.g., the slot angle (159) may be X degrees, and its opposite angle is 180–X, wherein X is 90 or less. This allows the guide pin (102) to be placed at a desired angle.

In some embodiments, the slot angle (159) is about 45 degrees. In some embodiments, the slot angle (159) is from 20 to 90 degrees. In some embodiments, the slot angle (159) is from 30 to 90 degrees. In some embodiments, the slot angle (159) is from 40 to 90 degrees. In some embodiments, the slot angle (159) is from 50 to 90 degrees. In some embodiments, the slot angle (159) is from 60 to 90 degrees. In some embodiments, the slot angle (159) is from 70 to 90 degrees. In some embodiments, the slot angle (159) is from 80 to 90 degrees.

In some embodiments, the slide bar (140) comprises more than one slot (150), and the slots are each at a different slot angle (159) with respect to the outer surface (144) of the slide bar (140). In some embodiments, the slide bar (140) comprises more than one slot (150), and the slots are each at the same slot angle (159) with respect to the outer surface (144) of the slide bar (140). In some embodiments, the slide bar (140) is removable and can be replaced with a different slide bar (140) having a slot (or more than one slot) having a different slot angle (159). This may allow the physician or health care worker to select a particular angle as needed.

In some embodiments, the system (100) further comprises a first guide wire locking component (not shown) for securing the guide wire (102) at a particular position within the slot (150) (with respect to the length of the slide bar (140), e.g., the distance between the guide wire (102) and the top end of the slot (150)). In some embodiments, the system (100) further comprises a second guide wire locking component (not shown) for securing the guide wire (102) at a particular angle within the slot (150) (with respect to the slide plate (140)).

Figure 6A:
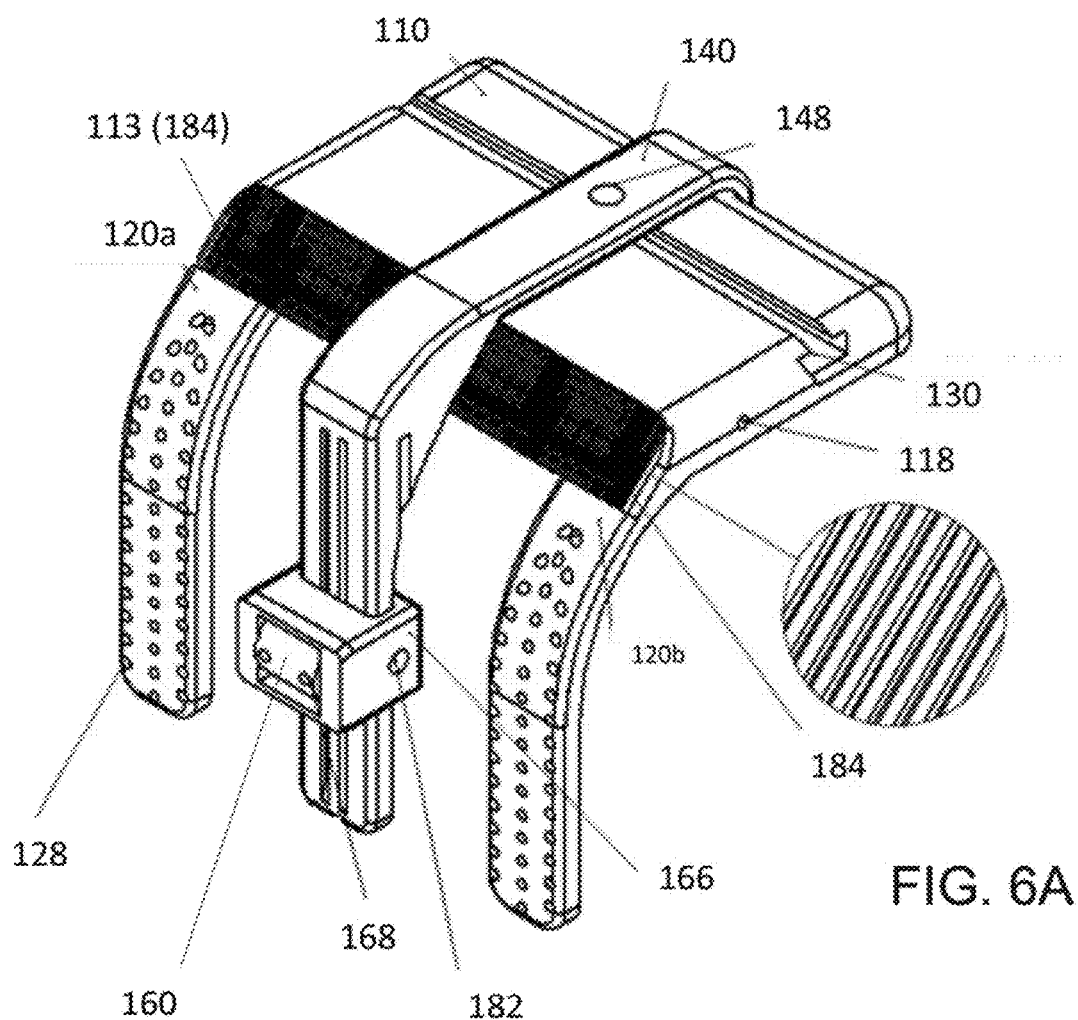
FIG. 6A shows a perspective view of an external angle guide system of the present invention.

FIG. 6A, FIG. 6B, FIG. 6C, FIG. 6D, and FIG. 6E show an alternative embodiment of a system (100) of the present invention. In some embodiments, the external guide system (100) of the present invention comprises an alignment plate (110) and one or more wings (120) that extend from the first side (113) (e.g., downwardly) from the first side (113) of the alignment plate (110), e.g., the wings (120) being positioned on opposite sides of the alignment plate (110). The system (100) may comprise a first wing (120a) and a second wing (120b) that extend downwardly (or downwardly and outwardly) from the first side (113) of the alignment plate (110). In some embodiments, at least a portion of the alignment plate (110) and/or wings (120) is coated with a gripping component (184). For example, as shown in FIG. 6A, a portion of the alignment plate (110) near the first side (113) is coated with a gripping component (184).

Figure 6B:
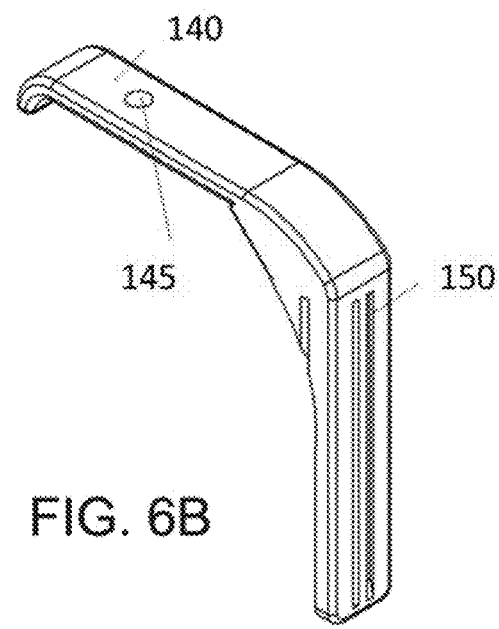
FIG. 6B shows a perspective view of a guide arm of the external angle guide system of FIG. 6A. The alignment plate is not shown in FIG. 6B.

In some embodiments, the system (100) further comprises a slide bar (140) adapted to engage with and slide in a channel (130) disposed in the top surface (115) of the alignment plate (110). (In some embodiments, a channel (130) may extend from at or near the first end (111) to at or near the second end (112) of the alignment plate (110). In some embodiments, the channel (130) extends through only a portion of the top surface (115) of the alignment plate (110).) In some embodiments, the slide bar (140) comprises a connector (148), which slidably engages the channel (130). As shown in FIG. 6B, the connector (148) may be disposed in a connector hole (145) in the slide bar (140). In some embodiments, the slide bar (140) can slide in at least a first direction toward the first end (111) of the alignment plate (110) and/or the first wing (120a) and a second direction toward the second end (112) of the alignment plate (110) and/or the second wing (120b). In some embodiments, the wings (120) limit the distance the sliding bar (140) can slide. In some embodiments, the slide bar (140) further comprises a locking component for securing the slide bar (140) in place within the channel (130). In some embodiments, the locking component is integrated into the connector (148) or is the connector (148) itself, e.g., the connector (148) functions as a locking component to temporarily secure the slide bar (140) in a particular place.

In some embodiments, a plurality of holes (128) (or channels) is disposed in the wings (120).

The holes (128) may be placed at an angle with respect to the outer surface (124) and/or inner surface (124) of the wing (120). The holes (128) may be configured in rows and/or columns. The holes (128) may be configured in pairs that are aligned in rows (e.g., a first hole is disposed in the first wing and a second hole is disposed in the second wing, and the two holes are aligned with one another with respect to the position along the length/height of the wing). The holes (128) are adapted to accept placement pins (105), e.g., placement pins (105) for inserting into the bone. In some embodiments, the holes of the pairs may be at different angles. However, the present invention is not limited to this configuration and the holes of the pair may be constructed at similar angles. In some embodiments, a user can choose two holes that are at two different angles, but the holes are not necessarily considered to be a pair (e.g., on the exact same row). The pairs of holes (e.g., channels through the wings) may be constructed having different angles. The wings are not limited to a single column of holes, e.g., the wings may have one, two, three, or more than three columns of holes. The wings (120) may each comprise one or more or a plurality of holes, and the holes may be at similar or different angles with respect to the outer surface (124) of the wing (120).

In some embodiments, an alignment bar (118) (e.g., a linear marking, groove, indentation, protrusion, etc.) is disposed in the top surface (115) of the alignment plate (110). In some embodiments, the alignment bar (118) extends from at or near the first end (111) to at or near the second end (112). In some embodiments, the alignment bar (118) extends through only a portion of the top surface (115) of the alignment plate (110). In some embodiments, the alignment bar (118) is a marking on one end of the alignment plate. In some embodiments, the alignment bar (118) is a pair of markings on opposite ends of the alignment plate (110). In some embodiments, the alignment bar (118) is intended to serve as a guide for placement of the system (100), wherein the alignment bar (118) is for aligning with the femur of the patient. In some embodiments, the alignment bar (118) is a groove or indentation. In some embodiments, the alignment bar (118) is a protrusion. In some embodiments, the alignment bar is a marking on the alignment plate (110).

As shown in FIG. 6A, FIG. 6C, FIG. 6D, and FIG. 6E, in some embodiments, a guide wire grip (160) is disposed on the slide bar (140) (e.g., via a guide wire grip base (166). The guide wire grip (160) functions to secure a guide wire (102) in a particular position and orientation. In some embodiments, the guide wire grip (160) comprises one or more guide wire grip holes (168) adapted to accept a guide wire (102) (and in some embodiments temporarily hold and secure a guide wire (102)). The guide wire grip (160) may be pivotally or rotatably attached to the slide bar (140) via a guide wire grip base (166). For example, in some embodiments, the guide wire grip (160) can pivot in a first direction and second direction with respect to the guide wire grip base (166) attached to the slide bar (140). In some embodiments, the guide wire grip base (166) is slidably attached to the slide bar (140). In some embodiments, the guide wire grip base (166) slidably engages one or more slots (150) on the slide bar (140). In some embodiments, a guide wire grip base channel (169) is disposed in the guide wire grip base (166), wherein the guide wire grip base channel (169) is adapted to accept the slide bar (140).

In some embodiments, the movement of the slide bar (140) along the channel (130), the movement of the guide wire grip base (166) along the slide bar (140), the pivoting of the guide wire grip (160) in the guide wire grip base (166), and the position of the guide wire grip holes (168) allow for many different positions, angles, and orientations of the guide wire with respect to the patient and the area of interest.

Figure 6C:
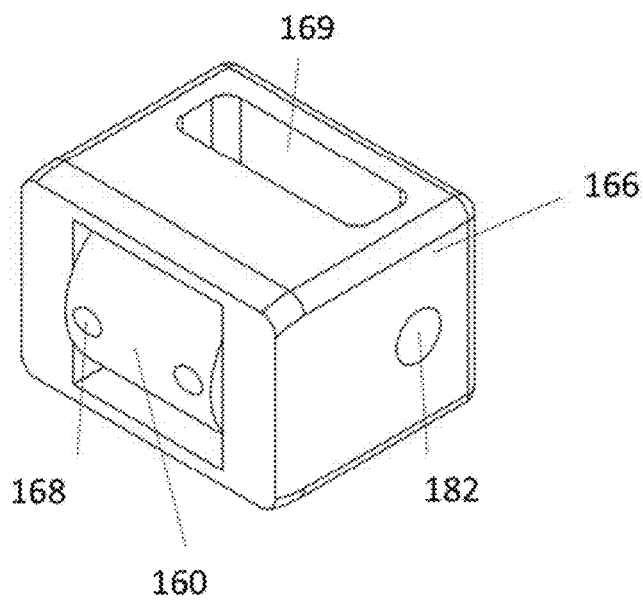
FIG. 6C shows a perspective view of a guide wire grip base of the external angle guide system of FIG. 6A (the guide arm and the alignment plate are not shown in FIG. 6C).
Figure 6D:
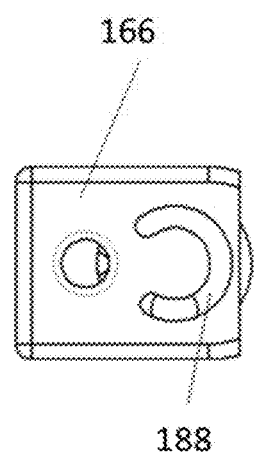
FIG. 6D shows a side view of the guide wire grip base of FIG. 6C.
Figure 6E:
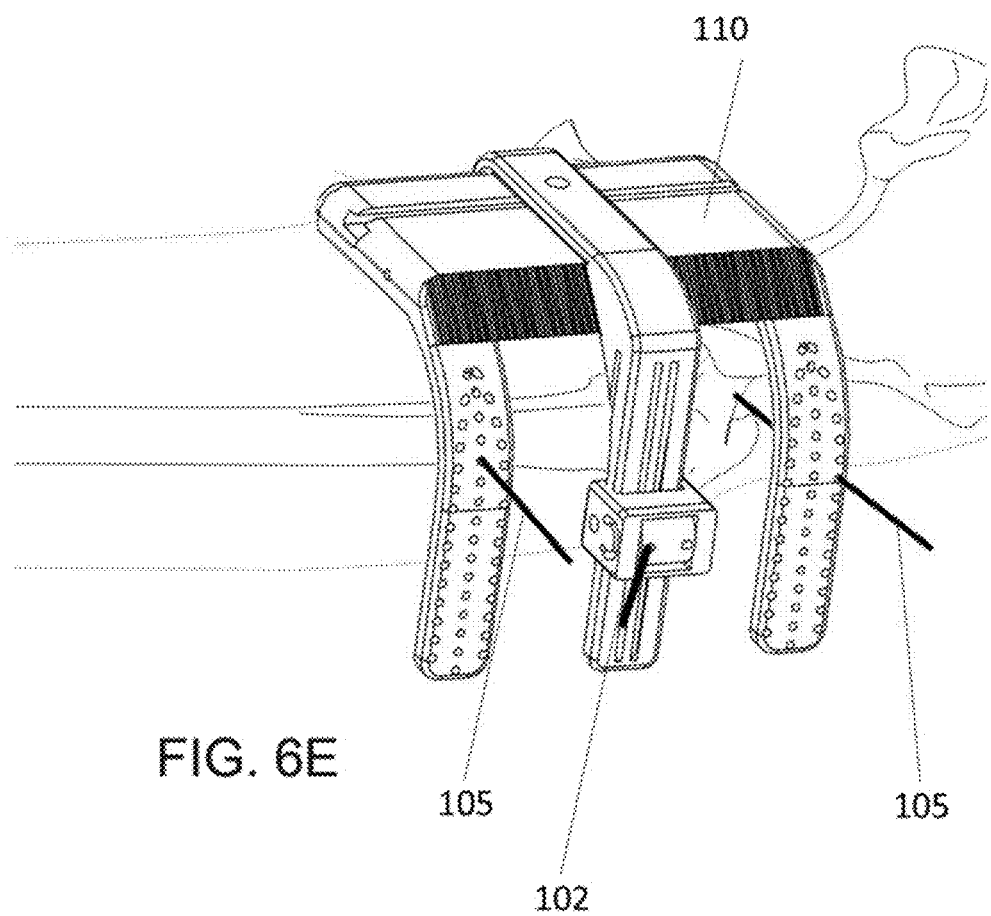
FIG. 6E shows an in-use view of the external angle guide system of FIG. 6A.

In some embodiments, a securing component or the slide bar (140) itself can temporarily secure the slide bar (140) in a position (e.g., desired position) with respect to the channel (130). In some embodiments, a securing component or the guide wire grip base (166) itself can temporarily secure the guide wire grip base (166) in a position (e.g., a desired position) with respect to the slide bar (140). In some embodiments, a securing component of the guide wire grip (160) itself can temporarily secure the guide wire grip (160) in a position (e.g., a desired position) with respect to the guide wire grip base (166). As shown in FIG. 6C and FIG. 6D, in some embodiments, the guide wire grip base (166) comprises an internal-external rotation screw fixation track (188) and tightening screw hole (182) for helping to secure the guide wire grip base (166) and/or guide wire grip (160) in a particular position.

Figure 7:
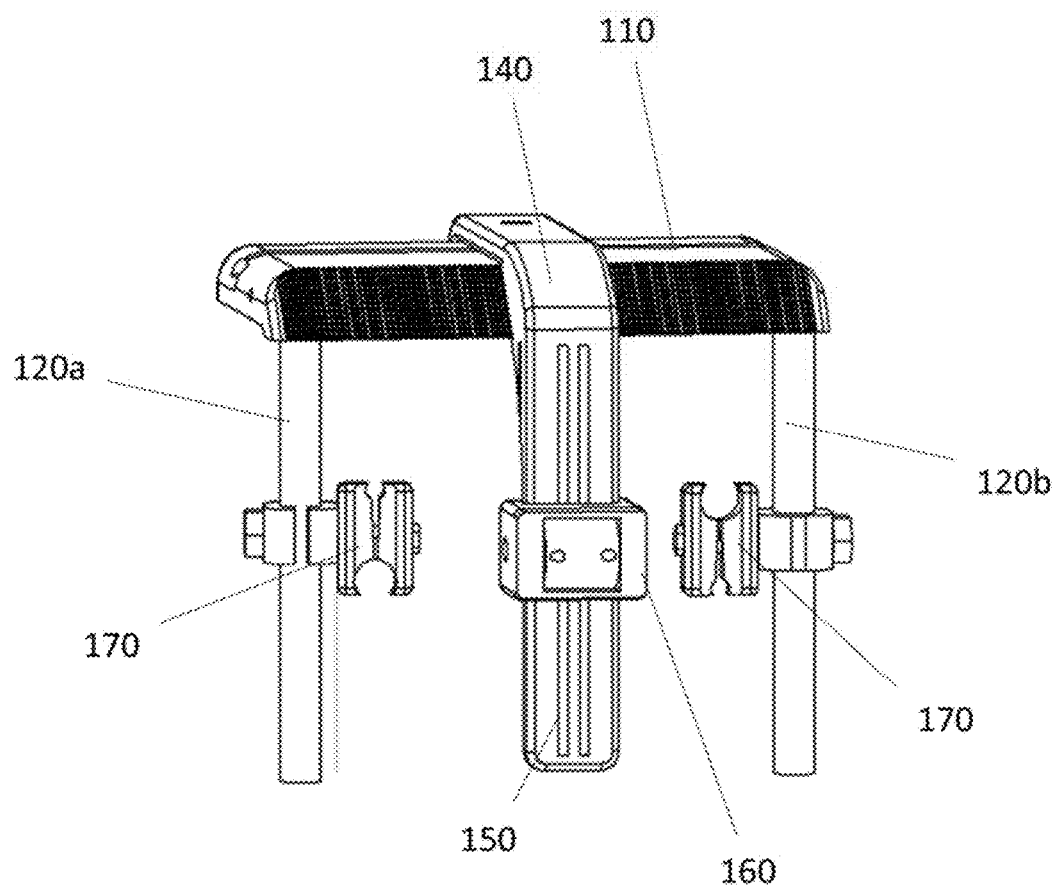
FIG. 7 shows a perspective view of an alternative embodiment of an external angle guide system of the present invention.

FIG. 7 shows an alternative embodiment of a system (100) of the present invention. In some embodiments, the external guide system (100) of the present invention comprises an alignment plate (110) and one or more wings (120) that extend from the first side (113) (e.g., downwardly) from the first side (113) of the alignment plate (110), e.g., the wings (120) being positioned on opposite sides of the alignment plate (110). The system (100) may comprise a first wing (120a) and a second wing (120b) that extend downwardly (or downwardly and outwardly) from the first side (113) of the alignment plate (110). In some embodiments, the wings (120) resemble shafts or cylinders, however the wings are not limited to a shaft or cylindrical configuration. In some embodiments, the wings (120) extend through wing channels in the alignment plate (110), e.g., the first wing (120a) extends through a first wing channel (120c) in the alignment plate (110), the second wing (120b) extends through a second wing channel (120d) in the alignment plate (110). In some embodiments, the wings (120) are perpendicular to the alignment plate (110). In some embodiments the wings (120) are at an angle with respect to the alignment plate (110), the angle being less than 90 degrees. In some embodiments, the wings (120) are at an angle with respect to the alignment plate (110), the angle being more than 90 degrees.

Slidably disposed on each wing (120) is a positioning pin grip (170) adapted to secure a positioning pin (105) in a particular location and orientation. In some embodiments, the positioning pin grip (170) is connected (slidably) to the wing (120) via a positioning pin grip base (176). The positioning pin grip base (176) (or the positioning pin grip (170) itself) may slide in a first direction and a second direction (e.g., upwardly, downwardly) along the wing (120) and may be secured in a particular position via a securing component. In some embodiments, the positioning pin grip base (176) functions as a clamp around the wing (120) (e.g., tightening the positioning pin grip base (176) may secure the positioning pin grip base (176) in place with respect to the wing (120)); however the positioning pin grip base (176) is not limited to this configuration. The positioning pin grip (170) comprises a positioning pin grip slot (172) adapted to accept a positioning pin (105). The positioning pin (105) may be secured within the positioning pin grip slot (172) via a securing component. In some embodiments, the positioning pin grip (170) (with slot (172)) functions as a clamp around the positioning pin (105) (e.g., tightening the positioning pin grip (170) may secure the positioning pin (105) in place with respect to the positioning pin grip slot (172)); however the positioning pin grip (170) is not limited to this configuration.

In some embodiments, the system (100) further comprises a slide bar (140) adapted to engage with and slide in a channel (130) disposed in the top surface (115) of the alignment plate (110). (In some embodiments, a channel (130) may extend from at or near the first end (111) to at or near the second end (112) of the alignment plate (110). In some embodiments, the channel (130) extends through only a portion of the top surface (115) of the alignment plate (110).) In some embodiments, the slide bar (140) comprises a connector (148), which slidably engages the channel (130). In some embodiments, the slide bar (140) can slide in at least a first direction toward the first end (111) of the alignment plate (110) and/or the first wing (120a) and a second direction toward the second end (112) of the alignment plate (110) and/or the second wing (120b). In some embodiments, the wings (120) limit the distance the sliding bar (140) can slide. In some embodiments, the slide bar (140) further comprises a locking component for securing the slide bar (140) in place within the channel (130). In some embodiments, the locking component is integrated into the connector (148) or is the connector (148) itself, e.g., the connector (148) functions as a locking component to temporarily secure the slide bar (140) in a particular place.

In some embodiments, a guide wire grip (160) is disposed on the slide bar (140) (e.g., via a guide wire grip base (166)). The guide wire grip (160) functions to secure a guide wire (102) in a particular position and orientation. In some embodiments, the guide wire grip (160) comprises one or more guide wire grip holes (168) adapted to accept a guide wire (102) (and in some embodiments temporarily hold and secure a guide wire (102)). The guide wire grip (160) may be pivotally or rotatably attached to the slide bar (140) via a guide wire grip base (166). For example, in some embodiments, the guide wire grip (160) can pivot in a first direction and second direction with respect to the guide wire grip base (166) attached to the slide bar (140). In some embodiments, the guide wire grip base (166) is slidably attached to the slide bar (140). In some embodiments, the guide wire grip base (166) slidably engages one or more slots (150) on the slide bar (140).

In some embodiments, the movement of the slide bar (140) along the channel (130), the movement of the guide wire grip base (166) along the slide bar (140), the pivoting of the guide wire grip (160) in the guide wire grip base (166), and the position of the guide wire grip holes (168) allow for many different positions, angles, and orientations of the guide wire with respect to the patient and the area of interest.

In some embodiments, a securing component or the slide bar (140) itself can temporarily secure the slide bar (140) in a position (e.g., desired position) with respect to the channel (130). In some embodiments, a securing component or the guide wire grip base (166) itself can temporarily secure the guide wire grip base (166) in a position (e.g., a desired position) with respect to the slide bar (140). In some embodiments, a securing component of the guide wire grip (160) itself can temporarily secure the guide wire grip (160) in a position (e.g., a desired position) with respect to the guide wire grip base (166). As shown in FIG. 6C and FIG. 6D, in some embodiments, the guide wire grip base (166) comprises an internal-external rotation screw fixation track (188) and tightening screw hole (182) for helping to secure the guide wire grip base (166) and/or guide wire grip (160) in a particular position.

The system (100) of the present invention may be constructed from a variety of materials. In some embodiments, all or a portion of the system (100) is constructed from a material that is generally radio-opaque. In some embodiments, all or a portion of the system (100) is constructed from a material that comprises acrylonitrile butadiene styrene (ABS); however, the present invention is not limited to a material comprising ABS.

The present invention also features methods (e.g., percutaneous methods) of positioning a guide wire in a bone at a desired position and orientation. The various degrees of freedom may be fixed independently. The present invention also features methods (e.g., percutaneous methods) of facilitating the treatment of a fracture (e.g., an IT fracture). In some embodiments, for example in an application related to facilitating treatment of a fracture such as an IT fracture, the method comprises utilizing an external angle guide system (100) of the present invention. For example, the external angle guide system (100) of the present invention may be placed atop a patient's leg, e.g., over the quadriceps area. In some embodiments, the alignment bar (118) may be aligned with the patient's femur. Placement pins (105) may be positioned and secured via positioning pin grip slots (172) in grips (170) along the wings (120). In some embodiments, the slide bar (140) is moved within the channel (130) of the alignment plate (110) to an appropriate position. In some embodiments, the slide bar (140) is secured with respect to the channel (130), e.g., via the connector (148) or via a locking component (144). As previously discussed, the present invention is not limited to use with respect to IT fractures. As such, the guide system (100) of the present invention may be placed on any appropriate treatment area of a patient that provides access to a particular bone for guide wire placement.

A guide wire (102) may be fed through the guide wire grip slot (162) (or slot (150)) as appropriate. For example, in some embodiments, the guide wire (102) is positioned at a particular position within the guide wire grip slot (162) at a particular angle via the guide wire grip (160), and at a particular height via the guide wire grip base (166) along the slide bar (140). In some embodiments, the guide wire (102) is secured in the guide wire grip slot (162) (or slot (150)) via various locking components or securing components. The present invention is not limited to the aforementioned steps.

In some embodiments of the present invention, a connection point between an alignment plate (110) and a slide bar (140) is disposed 2 cm to 5 cm from a guide wire entry point of the external guide system (100) of the present invention. The placement of the connector (148) near the guide wire entry point may provide enhanced stability and rigidity to the external guide system (100) of the present invention.

As previously discussed, the present invention features a percutaneous device and methods for placing a guide wire into a bone, e.g., placing a guide wire into the femoral head, wherein each degree of freedom is adapted to be controlled independently. As previously discussed, there are six degrees of freedom that may be required to fully specify the position and orientation of a body in 3D space, e.g., flexion/extension angle, varus/valgus angulation, internal/external rotation angle, superior/inferior position, anterior/posterior position, and medial/lateral position. As previously discussed, each degree of freedom may be controlled independently. As a non-limiting example, for example in the case of facilitating the treatment of an IT fracture, in some embodiments, the method comprises placing the device on a patient's thigh, aligning the v/v angulation, fixing the percutaneous device to the femur, selecting i/e rotation, fixing i/e rotation, selecting a/p position, and fixing the a/p position. X-ray images may be used (at one or more times during the process) to help verify placement of the guide position. In some embodiments, once the varus/valgus plane is fixed, the superior/inferior position may be addressed. In some embodiments, the ability to slide the guide wire (102) up and down with respect to the slide plate (140) may help to set the superior/inferior position. In some embodiments, x-ray images may be taken to observe that the guide wire (102) is at the correct superior/inferior position in the intertrochanteric fracture.

Figure 8A:
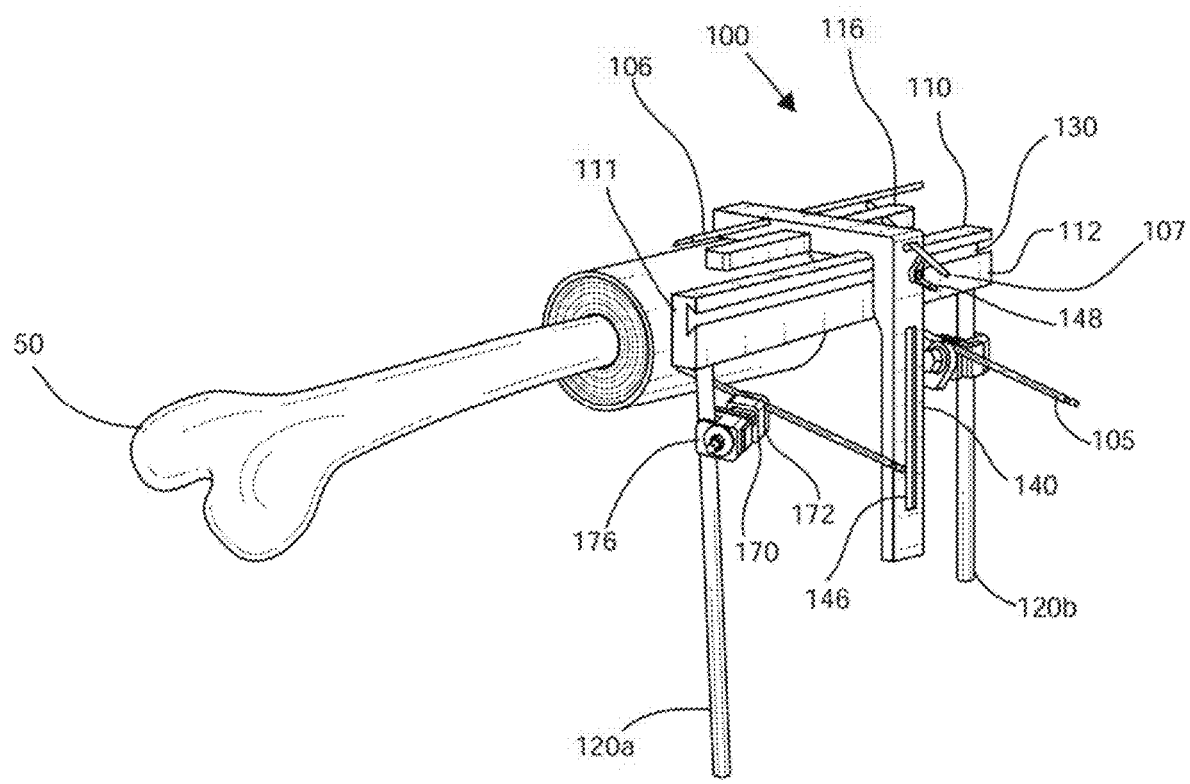
FIG. 8A shows a perspective view of a preferred embodiment of an external angle guide of the present invention.
Figure 8B:
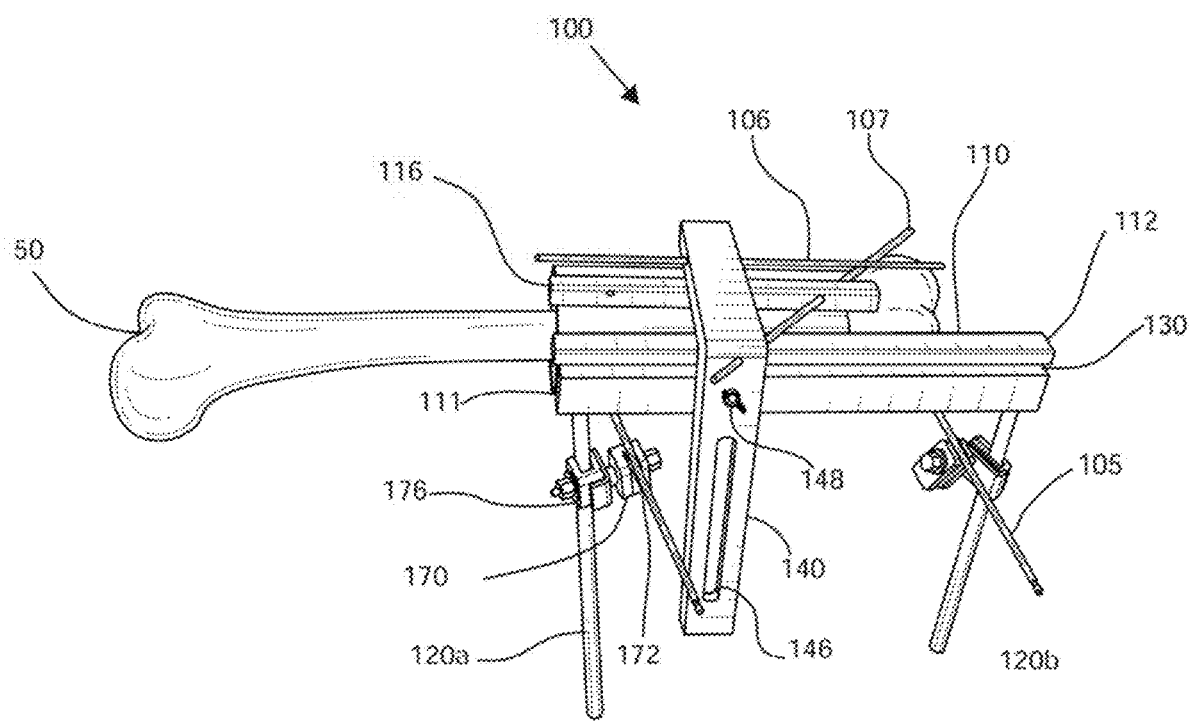
FIG. 8B shows a side view of the preferred embodiment of the external angle guide of FIG. 8A.
Figure 8C:
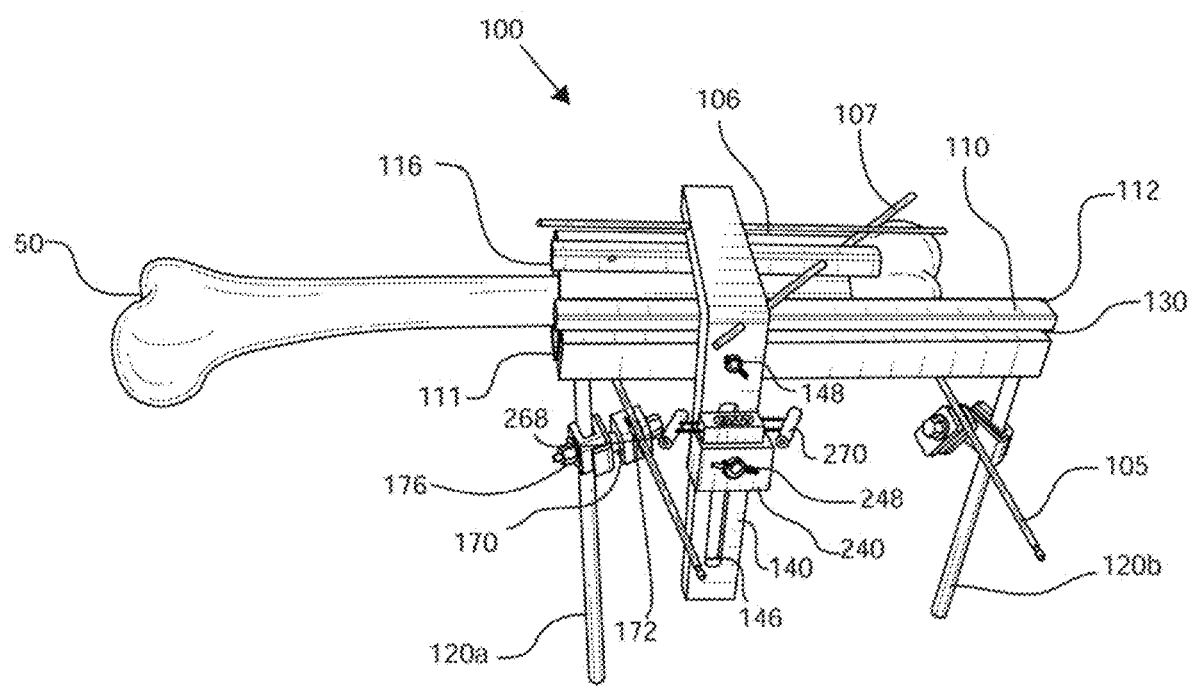
FIG. 8C shows a side view of the preferred embodiment of the external angle guide of FIG. 8A with an additional guiding component.

Referring now to FIGS. 8A-8C, the present invention features an external guide system (100) for placing a guide wire (102) into a bone at a particular position and orientation. The system (100) may comprise an alignment plate (110), a first wing (120a) and a second wing (120b) both extending downwardly from the alignment plate (110) on opposite sides. The system (100) may further comprise a positioning pin grip (170) slidably attached to each wing. The positioning pin grips (170) may be capable of sliding in a first direction toward the alignment plate (110) and a second direction opposite the first direction. Each positioning pin grip (170) may comprise a positioning pin grip slot (172) adapted to accept a placement pin (105). The system (100) may further comprise a slide bar (140) slidably engaged in a channel (130) disposed in the alignment plate (110). The slide bar (140) may extend downwardly from the alignment plate (110) and may slide in at least a first direction toward a first end (111) of the alignment plate (110) and a second direction toward a second end (112) of the alignment plate (110). The system (100) may further comprise a parallel guide pin (106) removably directed through a hole in the alignment plate (110) for determining whether or not the external guide system (100) is parallel to the bone. The system (100) may further comprise an upper angle guide (116) attached to the alignment plate (110) with an upper angle guide pin (107) removably directed through a hole in the alignment plate (110) and a hole in the upper angle guide (116) for determining a position of the slide bar (140) and a position of the external guide system (100). In some embodiments, the upper angle guide (116) rests on top of the bone. As seen in FIG. 8C, the system (100) may further comprise an additional guiding component (240) slidably and pivotably engaged in a slide bar channel (146). The additional guiding component (240) may comprise an additional guide wire hole (268) disposed therein adapted to position and hold the guide wire (102), an additional locking component (248), and an additional pre-positioning component (270). In some embodiments, an additional pre-positioning pin is removably directed through the additional pre-positioning component (270) for determining an angle and a channel position of the additional guiding component (240) in the slide bar channel (146). The guide wire (102) may be directed into the bone through the additional guide wire hole (268). The system (100) may be adapted to allow independent positioning of flexion-extension angle, varus-valgus angulation, internal-external rotation angle, superior-inferior position, anterior-posterior position, and medial-lateral position of the guide wire (102). In some embodiments, a connector (148) connects the alignment plate (110) to the slide bar (140) such that the connector (148) is disposed 2 cm to 5 cm from an entry point of the guide wire (102). In some embodiments, the additional pre-positioning component (270) is angled to direct the additional pre-positioning pin towards the bone at a 95 to 115 degree angle. In some embodiments, the additional guide wire hole (268) is angled to direct the guide wire (102) towards the bone at a 95 to 115 degree angle.

The system (100) of the present invention allows for a single parameter (e.g., v/v angulations) to be set prior the setting of a second parameter (e.g., s/I position), and adjustment of the second parameter may not necessitate the adjustment of the first parameter after it is set.

As used herein, the term "about" refers to plus or minus 10% of the referenced number.

The disclosures of the following patents/patent applications are incorporated in their entirety by reference herein: U.S. Pat. Nos. 6,562,042; 7,927,333; CN02215612; CN201310308203; CN201310072356; CN201320103500.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An external guide system (100) for placing a guide wire (102) into a bone at a particular position and orientation, said system (100) comprising:
   a. an alignment plate (110);
   b. a first wing (120a) and a second wing (120b) both extending downwardly from the alignment plate (110) on opposite sides;
   c. a positioning pin grip (170) slidably attached to each wing, the positioning pin grips (170) can be slid in a first direction toward the alignment plate (110) and a second direction opposite the first direction, wherein each positioning pin grip (170) comprises a positioning pin grip slot (172) adapted to accept a placement pin (105);
   d. a slide bar (140) slidably engaged in a channel (130) disposed in the alignment plate (110), the slide bar (140) extends downwardly from the alignment plate (110), the slide bar (140) can slide in at least a first direction toward a first end (111) of the alignment plate (110) and a second direction toward a second end (112) of the alignment plate (110);
   e. a parallel guide pin (106) removably directed through a hole in the alignment plate (110) for determining whether or not the external guide system (100) is parallel to the bone;
   f. an upper angle guide (116) attached adjacent to the alignment plate (110) with an upper angle guide pin (107) removably directed through a hole in the alignment plate (110) and a hole in the upper angle guide (116) for determining a position of the slide bar (140) and a position of the external guide system (100);
   g. an additional guiding component (240) slidably and pivotably engaged in a slide bar channel (146) and comprising an additional guide wire hole (268) disposed therein adapted to position and hold a guide wire (102), an additional locking component (248), and an additional pre-positioning component (270), wherein an additional pre-positioning pin is removably directed through the additional pre-positioning component (270) for determining an angle and a channel position of the additional guiding component (240), and wherein the guide wire (102) is directed into the bone through the additional guide wire hole (268);

wherein the system (100) is adapted to allow independent positioning of flexion-extension angle, varus-valgus angulation, internal-external rotation angle, superior-inferior position, anterior-posterior position, and medial-lateral position of the guide wire (102).

2. The system (100) of claim 1, wherein a connector (148) connects the alignment plate (110) to the slide bar (140) such that the connector (148) is disposed 2 cm to 5 cm from an entry point of the guide wire (102).

3. An external guide system (100) for placing a guide wire (102) into a bone at a particular position and orientation, said system (100) comprising:
   a. an alignment plate (110);
   b. at least a first wing (120*a*) extending downwardly from a first side (113) of the alignment plate (110), the first wing (120*a*) is adapted to directly or indirectly position and hold a placement pin (105);
   c. a positioning pin grip (170) adapted to position and hold a positioning pin (105) directly or indirectly slidably attached to the first wing (120*a*), the positioning pin grip (170) can be slid in a first direction toward the alignment plate (110) and a second direction opposite the first direction;
   wherein the positioning pin grip (170) is attached to a positioning pin grip base (176) which is slidably attached to the first wing (120*a*), the positioning pin grip base (176) slides in a first direction toward the alignment plate (110) and a second direction opposite the first direction;
   d. a slide bar (140) slidably engaged in a channel (130) disposed in the alignment plate (110), the slide bar (140) extends downwardly from the alignment plate (110), the slide bar (140) can slide in at least a first direction toward a first end (111) of the alignment plate (110) and a second direction toward a second end (112) of the alignment plate (110);
   d. a guide wire grip (160) adapted to position and hold a guide wire (102), the guide wire grip (160) is pivotally attached to a guide wire grip base (166) wherein the guide wire grip (160) can pivot within the guide wire grip base (166) in a first direction toward the alignment plate (110) and a second direction opposite the first direction, wherein the guide wire grip base (166) is slidably attached to the slide bar (140) such that it can slide in a first direction toward the alignment plate and a second direction opposite the first direction;
   wherein the system (100) is adapted to allow independent positioning of flexion-extension angle, varus-valgus angulation, internal-external rotation angle, superior-inferior position, anterior-posterior position, and medial-lateral position of the guide wire (102).

4. The system (100) of claim 3 further comprising a second wing (120*b*) extending downwardly from a second side (114) of the alignment plate (110) opposite the first side (113), the second wing (120*b*) is adapted to directly or indirectly accept a placement pin (105), the first wing (120*a*) and the second wing (120*b*) are separated by a distance, wherein the first wing (120*a*) comprises a plurality of holes (128) disposed therethrough that allow passage of a placement pin (105), the holes are at a first hole angle (129*a*) with respect to the length of the first wing (120*a*) and at a second hole angle (129*b*) with respect to the width of the first wing (120*a*), wherein the second wing (120*b*) comprises a plurality of holes (128) disposed therethrough that allow passage of a placement pin (105), the holes are at a first hole angle (129*a*) with respect to the length of the second wing (120*b*) and at a second hole angle (129*b*) with respect to the width of the second wing (120*b*), the first hole angle (129*a*) is from 20 to 90 degrees and the second hole angle (129*b*) is from 20 to 90 degrees.

5. The system (100) of claim 3, wherein the slide bar (140) comprises a guide wire grip shaft (164), wherein the guide wire grip base (166) is slidably attached to the guide wire grip shaft (164) and can slide in the first direction and second direction along the slide bar (140) via the guide wire grip shaft (164).

6. The system (100) of claim 3, wherein the guide wire grip base (166) engages a slot (150) disposed in the slide bar (140), the slot (150) extends along at least a part of a length of the slide bar (140).

7. A method of positioning a guide wire (102) into a bone at a particular position and orientation, said method comprising:
   a. placing an external guide system (100) atop a treatment area of a subject, said external guide system (100) comprising:
      i. an alignment plate (110);
      ii. a first wing (120*a*) and a second wing (120*b*) both extending downwardly from the alignment plate (110) on opposite sides;
      iii. a positioning pin grip (170) slidably attached to each wing, the positioning pin grips (170) can be slid in a first direction toward the alignment plate (110) and a second direction opposite the first direction, wherein each positioning pin grip (170) comprises a positioning pin grip slot (172) adapted to accept a placement pin (105);
      iv. a slide bar (140) slidably engaged in a channel (130) disposed in the alignment plate (110), the slide bar (140) extends downwardly from the alignment plate (110), the slide bar (140) can slide in at least a first direction toward a first end (111) of the alignment plate (110) and a second direction toward a second end (112) of the alignment plate (110);
      v. a parallel guide pin (106) removably directed through a hole in the alignment plate (110) for determining whether or not the external guide system (100) is parallel to the bone;
      vi. an upper angle guide (116) attached adjacent to the alignment plate (110) with an upper angle guide pin (107) removably directed through a hole in the alignment plate (110) and a hole in the upper angle guide (116) for determining a position of the slide bar (140) and a position of the external guide system (100);
      vii. an additional guiding component (240) slidably and pivotably engaged in a slide bar channel (146) and comprising an additional guide wire hole (268) disposed therein adapted to position and hold a guide wire (102), an additional locking component (248), and an additional pre-positioning component (270), wherein an additional pre-positioning pin is removably directed through the additional pre-positioning component (270) for determining an angle and a channel position of the additional guiding component (240), and wherein the guide wire (102) is directed into the bone through the additional guide wire hole (268);
      viii. a guide wire grip (160) adapted to position and hold the guide wire (102), the guide wire grip (160) is pivotally attached to a guide wire grip base (166) wherein the guide wire grip (160) can pivot within the guide wire grip base (166) in a first direction toward the alignment plate (110) and a second direction opposite the first direction, wherein the guide wire grip base (166) is slidably attached to the slide bar (140) such that it can slide in a first direction toward the alignment plate and a second direction opposite the first direction; wherein the system (100) is adapted to allow independent positioning of flexion-extension angle, varus-valgus angulation, internal-external rotation angle, superior-inferior position, anterior-posterior position, and medial-lateral position of the guide wire (102);

b. positioning at least one placement pin (105) directly or indirectly in the first wing (120*a*) and further into the bone to secure the external angle guide system (100) in place;

c. positioning the slide bar (140) to an appropriate position within the channel (130) using a plurality of guiding pins positioned relative to the bone using a plurality of x-ray images; and d. inserting the guide wire (102) through the guide wire grip (160) and further into a bone.

8. The method of claim 7 further comprising pivoting the guide wire grip (160) within the guide wire grip base (166) to help position the guide wire (102).

9. The method of claim 7 further comprising sliding the guide wire grip base (166) on the slide bar (140) to help position the guide wire (102).

10. The method of claim 7 further comprising securing the slide bar (140) in the channel (130) via a locking component (144) such that the locking component (130) is disposed 2 cm to 5 cm from an entry point of the guide wire (102).

11. The method of claim 7, wherein the method is for facilitating the treatment of a fracture or an osteotomy.

* * * * *